(12) United States Patent
Groen et al.

(10) Patent No.: US 7,658,925 B2
(45) Date of Patent: Feb. 9, 2010

(54) HUMAN ANTHRAX TOXIN NEUTRALIZING MONOCLONAL ANTIBODIES AND METHODS OF USE THEREOF

(75) Inventors: Herman Groen, Groningen (NL);
Christine Cool-Kebbedies, Groningen (NL); Kunja S. Slopsema, Drachten (NL); Hans Westra, Zwaagwesteinde (NL)

(73) Assignee: IQ Therapeutics BV (NL)

( * ) Notice: Subject to any disclaimer, the term of this patent is extended or adjusted under 35 U.S.C. 154(b) by 615 days.

(21) Appl. No.: 11/072,102

(22) Filed: Mar. 3, 2005

(65) Prior Publication Data

US 2006/0258842 A1    Nov. 16, 2006

Related U.S. Application Data

(60) Provisional application No. 60/549,641, filed on Mar. 3, 2004.

(51) Int. Cl.
*A61K 39/40* (2006.01)
*C12N 5/06* (2006.01)

(52) U.S. Cl. ............... 424/164.1; 424/150.1; 530/388.4; 530/388.1; 435/70.1; 435/326; 435/252.3

(58) Field of Classification Search ................ None
See application file for complete search history.

(56) References Cited

U.S. PATENT DOCUMENTS

| 7,262,019 | B2 * | 8/2007 | Kovalenko | 435/7.5 |
|---|---|---|---|---|
| 2004/0009178 | A1 | 1/2004 | Bowdish et al. | 424/164.1 |
| 2004/0258699 | A1 * | 12/2004 | Bowdish et al. | 424/184.1 |

FOREIGN PATENT DOCUMENTS

| WO | WO 03/037370 A2 | 5/2003 |
|---|---|---|
| WO | WO 2005/023177 A2 | 3/2005 |
| WO | 2005/056052 * | 6/2005 |
| WO | WO 2005/081749 A2 | 9/2005 |

OTHER PUBLICATIONS

Quinn et al (Emerging Infectious Diseases 8(10):1103-1110, Oct. 2002.*
Campbell et al, Monoclonal Antibody Immunosensor Technology, Elseveir, 1991, Chapter 1, pp. 1-49, p. 3 in particular.*
Harlow et al In Antibodies A Laboratory Manual, Cold Spring Harbor Press, 1988, Chapter 3, pp. 23-35.*
Herbert, Dictionary of Immunology 4th Ed, Academic Press, 1995 pp. 58-59.*
Greenbaum et al, Journal of Molecular Recognition, 20(2):75-82, 2007.*
Greenspan et al (Nature Biotechnology 7:936-937 (1999)).*
Little et al, (Infection and Immunity, 58(6):1606-1613, 1990).*
Zhao et al (Human Antibodies, 12:129-135, 2003).*
Cirino et al. *Infect. Immunol.*, 67(6):2957-2963 (1999).
Davies et al. *Immunotech.*, 2:169-179 (1996).
Holt et al. *TRENDS Biotechnol.*, 21(11):484-490 (2003).
International Search Report for PCT/IB2005/002495, mailed Dec. 7, 2005.
Balint et al., "Antibody engineering by parsimonious mutagenesis", *Gene*, 137, 109-118(1993).

* cited by examiner

*Primary Examiner*—Patricia A Duffy
(74) *Attorney, Agent, or Firm*—Mintz, Levin, Cohn, Ferris, Glovsky and Popeo, P.C.; Cynthia A. Kozakiewicz

(57) ABSTRACT

The invention fully humanized monoclonal antibodies that neutralize *Bacillus anthracis*. Also provided are methods of treating or preventing a *Bacillus anthracis* infection. The invention also provides methods of passive vaccination of a subject against *Bacillus anthracis*.

10 Claims, 13 Drawing Sheets

HUMAN ANTHRAX TOXIN NEUTRALIZING MONOCLONAL ANTIBODIES AND METHODS OF USE THEREOF

RELATED APPLICATIONS

This application claims priority to U.S. Ser. No. 60/549,641 filed Mar. 3, 2004 and which is incorporated herein by reference in its entirety.

FIELD OF THE INVENTION

This invention relates generally to anti-anthrax antibodies as well as to methods for use thereof.

BACKGROUND

*Bacillus anthracis*, the virulent, endospore-forming bacterium notorious for its recent use as a bioterror weapon, has plagued humans and livestock from antiquity (Friedlander 2000). The bacterium was associated with the founding of the sciences of bacteriology and immunology, highlighted by Pasteur's famous demonstration of vaccine protection of sheep at Pouilly-le-Fort, France. Since then, the attention *Bacillus anthracis* has received has largely revolved around its properties that make it ideally suited as a biological weapon as it forms heat resistant spores that are easy to produce and to transport, and can infect via the aerosol route.

SUMMARY OF THE INVENTION

The invention is based in part upon the discovery of fully human anthrax toxin neutralizing monoclonal antibodies. The monoclonal antibody (mAb) binds to *Bacillus anthracis* protective antigen (PA) polypeptide or the lethal factor (LF) polypeptide and neutralizes lethal toxin (LeTx). Exemplary monoclonal antibodies include IQNPA and IQNLF described herein.

An IQNPA antibody contains a heavy chain polypeptide having the amino acid sequence of SEQ ID NO:2 or fragment thereof and nucleic acid sequence of SEQ ID NO:1 or fragment thereof. Preferably, the IQNPA antibody heavy chain polypeptide has the amino acid sequence of amino acid residues 1-106 of SEQ ID NO:2 and more preferably amino acid residues 31-106 of SEQ ID NO:2. An IQNPA antibody contains a light chain polypeptide having the amino acid sequence of SEQ ID NO:4 or fragment thereof and nucleic acid sequence of SEQ ID NO:3 or fragment thereof. Preferably, the IQNPA antibody light chain polypeptide has the amino acid sequence of amino acid residues 1-97 of SEQ ID NO:2 and more preferably amino acid residues 24-97 of SEQ ID NO:2.

An IQNLF antibody contains a heavy chain polypeptide having the amino acid sequence of SEQ ID NO:6 or fragment thereof and nucleic acid sequence of SEQ ID NO:5 or fragment thereof. Preferably, the IQNLF antibody heavy chain polypeptide has the amino acid sequence of amino acid residues 1-106 of SEQ ID NO:6 and more preferably amino acid residues 31-106 of SEQ ID NO:6. An IQNLF antibody contains a light chain polypeptide having the amino acid sequence of SEQ ID NO:8 or fragment thereof and nucleic acid sequence of SEQ ID NO:7 or fragment thereof. Preferably, the IQNLF antibody light chain polypeptide has the amino acid sequence of amino acid residues 1-97 of SEQ ID NO:2 and more preferably amino acid residues 24-97 of SEQ ID NO:2.

Also included in the invention is an isolated fully human monoclonal antibody or fragment thereof having a heavy chain with three CDRs containing the amino acid sequence of KKPGA (SEQ ID NO:11); SNAIQWVRQAPGQRLEW (SEQ ID NO:12); YMELSSLR (SEQ ID NO:13) or a light chain with three CDRs containing the amino acid of LTQSPGTLSLS (SEQ ID NO:14); SYSSLAW (SEQ ID NO:15); GPDFTLTIS (SEQ ID NO:16). The antibody binds to an epitope on a region of the protective antigen polypeptide and neutralizes *Bacillus anthracis* lethal toxin polypeptide.

Additionally, the invention provides an isolated fully human monoclonal antibody or fragment thereof, having a heavy chain with three CDRs conatining the amino acid sequence of VQPGG (SEQ ID NO:17); SYAM-SWVRQAPGKGLEW (SEQ ID NO:18); YMQMNSL (SEQ ID NO:19), or a light chain with three CDRs containing the amino acid sequence of TQSPDFQSVSP (SEQ ID NO:20); SSLHWYQ (SEQ ID NO:21); DFTLTINSL (SEQ ID NO:22). The antibody binds to an epitope on a region of the lethal factor polypeptide and neutralizes the *Bacillus anthracis* lethal toxin.

Alternatively, the monoclonal antibody is an antibody that binds to the same epitope as IQNPA, or IQNLF. For example, the antibody competes with the binding of monoclonal antibody IQNPA to domain 4 of a protective antigen polypeptide or with IQNLF to a LF polypeptide.

By binding to protective antigen is meant that the monoclonal antibody specifically interacts with a portion of the protective antigen polypeptide. For example, the monoclonal antibody binds to domain 4 of a protective antigen polypeptide. By binding to LF is meant that the mAb specifically interacts with a portion of the LF polypeptide. By specific interaction it is meant that the monoclonal antibody has a binding affinity said binding affinity from about $10^{-6}$ M to about $10^{-14}$ M. Preferably, the binding affinity is from about $10^{-8}$ M to about $10^{-12}$ M. For example, the binding affinity is about $10^{-10}$ M. Binding affinity is measured by methods known in the art.

Neutralizing lethal toxin is defined by an increase in cell survival after exposure to *Bacillus anthracis*. For example a the monoclonal antibody decreases complex formation between protective antigen and lethal factor (LF) or edema factor (EF), thereby decreasing the translocation of LF and EF into the cellular cytosol.

Optionally, the monoclonal antibody inhibits binding of (i) PA to target cells, (ii) PA to the anthrax toxin receptor (ATR) or (iii) lethal factor to protective antigen. Alternatively, the mAb inhibits the binding of PA to PA thus preventing heptamerization.

The monoclonal antibody is 2, 4, 8, 10, 15, 20, 25 or more times effective at neutralizing *Bacillus anthracis* lethal toxin polypeptide compared to a naturally occuring *Bacillus anthracis* antisera. A naturally occuring *Bacillus anthracis* antisera is for example derived from subjects immunized with an anthrax vaccine such as AVA or AVP. Exemplary *Bacillus anthracis* antisera includes AVR414.

The invention also features methods of preventing or reducing the risk of developing a *Bacillus anthracis* infection in a subject by identifying a subject at risk of developing *Bacillus anthracis* infection and administering to the subject a composition containing a human monoclonal antibody of the invention such as IQNPA, IQNLF or a combination thereof.

The invention further features methods of alleviating a symptom of a *Bacillus anthracis* infection in a subject by identifying a subject suffering from a *Bacillus anthracis* infection and administering to the subject a composition containing a human monoclonal antibody of the invention such as an IQNPA or IQNLF antibody. Optionally, the subject is further administered an antibiotic such as ciprofloxacin, doxycycline, amoxicillin, or penicillin G procaine.

Also included in the invention is a method for passive immunization a subject against *Bacillus anthracis*, by administering to a subject a composition containing the monoclonal antibody of the invention such as IQNPA or IQNLF mAbs.

The monoclonal antibody is administered before exposure to *Bacillus anthracis*. For example, the monoclonal antibody is administered at least 1 year before *Bacillus anthracis* exposure. The monoclonal antibody is administered 1 day, 2 days, 3 days, 4 days, 5 days, 6 days, 1 week, 2 weeks, 3 weeks, 1 month, 2 months, 3 months or more before exposure to *Bacillus anthracis*. Alternatively, the monoclonal antibody is administered after exposure to *Bacillus anthracis*. For example, the monoclonal antibody is administered at least 1 hour, 2 hours, 3 hours, 4 hours, 8 hours or more after *Bacillus anthracis* exposure. The monoclonal antibody is administered 1 day, 2 days, 3 days, 4 days or more after exposure to *Bacillus anthracis*.

The subject is suffering from or at risk of developing to *Bacillus anthracis* infection. The subject is a mammal such as a human, a primate, mouse, rat, dog, cat, cow, horse, pig.

A subject suffering from or at risk of developing *Bacillus anthracis* is identified by methods known in the art, e.g., by isolating *B. anthracis* from the blood, skin lesions, or respiratory secretions or by measuring specific antibodies in the blood. Symptoms of *B. anthracis* infection include fever (temperature greater than 100 degrees F.), chills or night sweats, flu-like symptoms, cough, usually a non-productive cough, chest discomfort, shortness of breath, fatigue, muscle aches, sore throat, followed by difficulty swallowing, enlarged lymph nodes, headache, nausea, loss of appetite, abdominal distress, vomiting, or diarrhea or in the case of cutaneous contraction, a sore, especially on the face, arms or hands, that starts as a raised bump and develops into a painless ulcer with a black area in the center.

The invention further provides a method of detecting the presence of a *Bacillus anthracis* bacterium in a sample, by contacting a sample known to or suspected of containing a *Bacillus anthracis* bacterium with the monoclonal antibody according to the invention and detecting the presence or absence of an antibody-bacterium complex. The presence of an antibody-bacterium complex indicates the sample contains a *Bacillus anthracis* bacterium. In contrast, the absence of an antibody-bacterium complex indicates the sample does not contains a *Bacillus anthracis* bacterium. The sample is for example blood, a skin lesion, a respiratory secretions, vesicular fluid or cerebrospinal fluid. The sample is contacted with the monoclonal antibody in vitro or in vivo. The monoclonal antibody is for example IQNPA or IQNLF. Optionally, the monoclonal antibody is labeled.

Also provided is a composition, and a passive vaccine composition containing the monoclonal antibody according to the invention and a carrier. The invention also includes a kit containing in one or more containers, the monoclonal antibody according to the invention.

In another aspect, the invention provides an isolated nucleic acid molecule that includes the sequence of SEQ ID NO:1, SEQ ID NO:3, SEQ ID NO:5 or SEQ ID NO:7 or fragment, homolog, analog or derivative thereof. The nucleic acid can include, e.g., a nucleic acid sequence encoding a polypeptide at least 99% identical to a polypeptide that includes the amino acid sequences of SEQ ID NO:2, SEQ ID NO:4, SEQ ID NO:6 or SEQ ID NO:8 or a nucleic acid sequence encoding a polypeptide at least 95% identical to a polypeptide that includes the amino acid sequences of SEQ ID NO:2, SEQ ID NO:4, SEQ ID NO:6 or SEQ ID NO:8. The nucleic acid can be, e.g., a genomic DNA fragment, or a cDNA molecule. Preferably, the nucleic acid is naturally occurring. The invention also provides a nucleic acid sequence that is complementary to the nucleic acid sequence of SEQ ID NO:1, SEQ ID NO:3, SEQ ID NO:5 or SEQ ID NO:7.

Also included in the invention is a vector containing one or more of the nucleic acids described herein, and a cell containing the vectors or nucleic acids described herein.

In another aspect, the invention provides an isolated polypeptides that includes the sequence of SEQ ID NO:2, SEQ ID NO:4, SEQ ID NO:6 or SEQ ID NO:8 or fragment, homolog, analog or derivative thereof. The polypeptide can include, e.g., an amino acid sequence at least 99% identical to a polypeptide of SEQ ID NO:2, SEQ ID NO:4, SEQ ID NO:6 or SEQ ID NO:8 or a a polypeptide at least 95% identical to a polypeptide that includes the amino acid sequences of SEQ ID NO:2, SEQ ID NO:4, SEQ ID NO:6 or SEQ ID NO:8.

The invention is also directed to host cells transformed with a vector comprising any of the nucleic acid molecules described above.

Also included in the invention is the hybridoma cell line which was deposited at the American Type Tissue Collection and assigned ATCC designation _____, _____, _____, or _____ and the monoclonal antibodies produced the hybridoma cell lines.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 2 is a bar chart depicting the results of an anthrax toxin neutralization assay (second experiment) showing that IQNPA-1 and IQNPA-2 are effective at neutralizing toxin in vitro.

FIG. 3 is a bar chart depicting the results of an anthrax toxin neutralization assay showing that IQNPA-1 and IQNPA-2 are effective at neutralizing toxin in vitro after PA had been allowed to bind target cells for 2 hours.

FIG. 4 is a bar chart depicting the results of an anthrax toxin neutralization assay showing that IQNPA-1 and IQNPA-2 are effective at neutralizing toxin in vitro after PA had been allowed to bind target cells for 3 hours.

FIG. 5 is a bar chart depicting the results of an in vitro anthrax toxin neutralization assay showing that IQNLF-1 and IQNLF-2 are effective at neutralizing toxin in vitro.

DETAILED DESCRIPTION OF THE INVENTION

Figure 1:
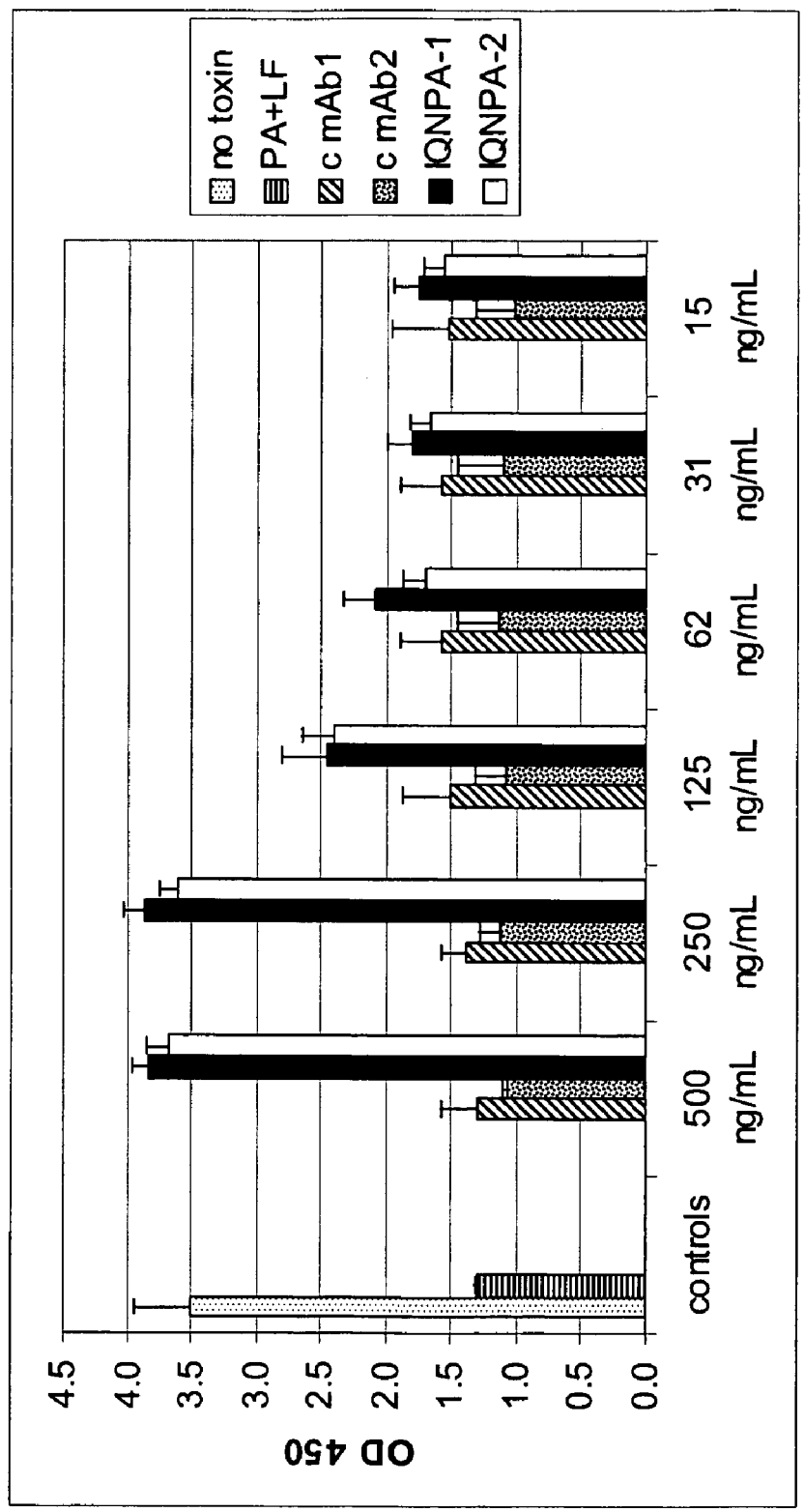
FIG. 1 is a bar chart depicting the results of an anthrax toxin neutralization assay (first experiment) showing that IQNPA-1 and IQNPA-2 are effective at neutralizing toxin in vitro.
Figure 6:
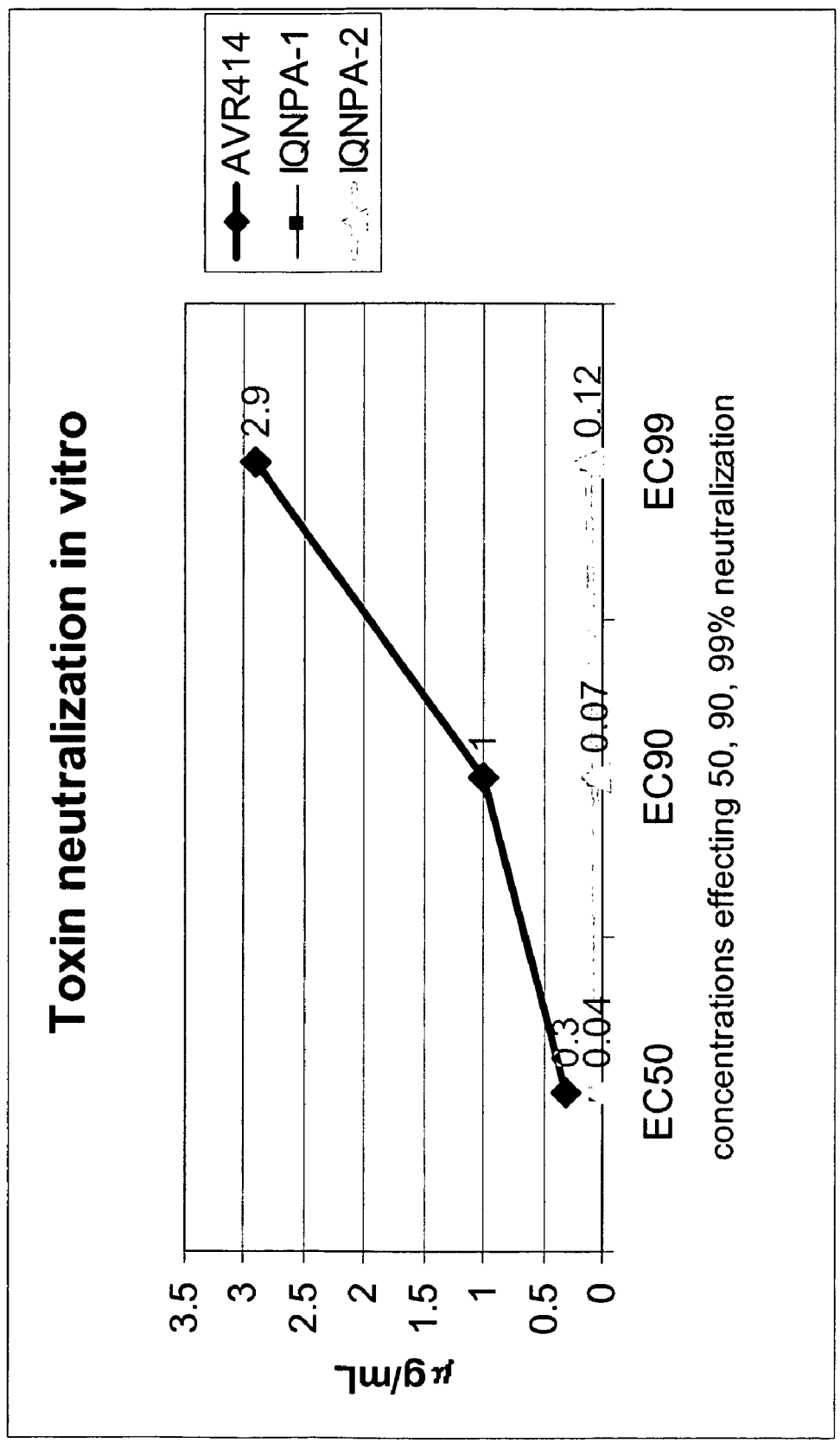
FIG. 6 is a bar chart depicting the results of an in vivo anthrax toxin neutralization assay measured after pre-incubation of target cells and protective antigen showing that IQNPA-1 and IQNPA-2 are effective at neutralizing toxin in vivo.

The present invention is based in part upon the discovery of fully human monoclonal antibodies, IQNPA-1 and IQNPA-2, which are specific for *B. anthracis* protective antigen (PA) and IQNLF-1 and IQNLF-2 which are specific for *B. anthracis* lethal factor (LF). Sequence analysis of IQNPA-1 and IQNPA-2 revealed that the two antibodies have identical nucleic acid sequences, thus are derived from the same primary clone. Similar results were found for IQNLF-1 and IQNLF-2. Accordingly, the terms IQNPA-1 and IQNPA-2 and IQNLF-1 and IQNLF-2 are used interchangeably and the antibodies are respectively referred to herein is IQNPA and IQNLF antibodies. Hybridoma cells lines producing IQNPA-1 and IQNPA-2 and IQNLF-1 and IQNLF-2 human monoclonal antibodies are designated IQNPA-1 and IQNPA-2 and IQNLF-1 and IQNLF-2 hybridomas respectively. The IQNPA and IQNLF antibodies are collectively referred to herein as IQN antibodies or huMabs. A deposit of the hybridoma cell lines IQNPA-1 and IQNPA-2 and IQNLF-1 and IQNLF-2 was made at the American Type Tissue Collection, 12301 Parklawn Drive, Rockville Md. 20852, on _____, and given the ATCC designations _____, _____, _____, and _____ respectively.

IQNPA antibodies neutralize *Bacillus anthracis'* Lethal Toxin in vivo and in vitro. Similarly, IQNLF antibodies neutralize *Bacillus anthracis'* Lethal Toxin in vitro. In addition, the IQNPA antibodies bind to the anthrax toxin receptor (ATR) binding site of the PA polypeptide. In mice exposed to the IQNPA antibodies prior to *B. anthracis* challenge it was found that the antibody treatment protected 50% of the animals exposed at dosages as low as 2.7 and 4.8 µg/mL, which approximately compares to 0.125 and 0.25 mg/kg respectively. Moreover, IQNPA antibodies provided 100% protection when administered up to 36 hrs after exposure to 25-40× MLD *Bacillus anthracis* spores. In contrast, in untreated mice the average time-to-death after exposure to these spores is about 55 hrs (2.3 days). These results demonstrate that IQNPA antibodies are useful for both post-exposure and prophylactic treatment of anthrax infection.

*B. anthracis* is a Gram-positive aerobic, spore-forming, rod-shaped bacterium. *B. anthracis* has two major virulence factors, a tripartite toxin and an anti-phagocytic capsule. The three proteins of the exotoxin are oedema factor (EF), lethal factor (LF) and protective antigen (PA). EF and LF enzymatically modify substrates within the cytosol of mammalian cells; EF is an adenylate cyclase that causes fluid loss from affected tissues and inhibition of phagocytosis and LF is a zinc-dependent protease that cleaves mitogen-activated protein kinase kinase and causes lysis of macrophages PA derives its name from the fact that it is the key protective immunogen in the current human vaccines. PA binds to the anthrax toxin receptor (ATR), whereupon a 20 kDa fragment is cleaved off, allowing the remaining 63 kDa carboxy-terminal part to form a membrane-inserting heptamer that binds one to three of the toxic enzymes, LF, to form lethal toxin (LeTx) or EF, to form edema toxin (ET), and translocate the toxic enzymes into the cytosol. LeTx is the major contributor to virulence in infected animals, which appears to be the central effector of shock and death from systemic anthrax Man generally acquires the disease directly, from contact with infected livestock or indirectly in industrial occupations concerned with processing animal products. There are three forms of the disease that are recognised in humans: cutaneous, inhalational and gastrointestinal infection. The inhalational form is of most concern in the context of biological attack. Following inhalation, spores are phagocytosed by alveolar macrophages and transported to draining lymph nodes, where the spores germinate and multiplication of vegetative bacilli occurs. Fatal bacteraemia and toxaemia then ensue, with a mortality rate in untreated individuals of >80%. Early treatment is essential as animal studies suggests that the disease reaches a point at which antibiotics are no longer effective due to the accumulation of a lethal level of toxin even though the organism is sensitive to the agent.

Currently, the US licensed human vaccine (AVA) stimulates antibodies which neutralize the activity of anthrax toxin (Ivins et al. 1998). However, it has been shown that it can take several weeks to mount a significant toxin neutralizing antibody response. Thus, active immunization is unlikely to be affective within the time frame on an infection. An alternative approach would be to administer preformed lethal toxin neutralizing antibodies. It has been demonstrated across a number of animal studies that preformed antibodies from animals (e.g., horse) immunized with anthrax vaccine or PA can passively protect recipients including humans. However, there are disadvantages to using animal derived sera. Access is dependant on the continuous availability of well-immunized, well-maintained and well-controlled animals. The concentration, efficacy and safety of the material is variable and uncontrollable. Furthermore, animal derived sera can only be used effectively for a limited period of time as a neutralizing antibody response will be mounted against the animal antibodies after prolonged or repeated usage. More seriously, is the fact that human recipients may react adversely to the serum, ranging from serum sickness to anaphylactic shock, or may contract one of a number of animal pathogens lethal to humans.

An improvement would be to use polyclonal antibodies collected from humans who have been immunized with the licensed human anthrax vaccine (AVA). The advantage of using human-derived sera is that human sera are less immunogenic than animal sera, thus there will be a reduced neutralizing antibody response enabling prolonged and repeated usage and a probable reduction in adverse responses. In addition, human IgG has a serum half life of 20 days, one infusion of human antibody could theoretically protect an exposed individual for several weeks However, the major disadvantages of this approach, are the risk of disease transmission, the batch to batch variations in concentrations of the active ingredients and therefore efficacy of the material and the inability to raise sufficient amounts of protective sera (with sufficiently high titers) to protect all people exposed in the event of a biological warfare or bioterrorist attack.

Alternatively, the best approach would be to develop human anthrax toxin neutralizing monoclonal antibodies which could be used to treat infected individuals and/or to provide "short term cover" to unprotected individuals who are in or will be deployed into high risk environments. Further advantages would be the reduced need to take prophylactic antibiotics, the long term use of which can cause considerable gasterointestinal dysfunctions well as the antibodies being effective against antibiotic resistant anthrax strains. Accordingly, human monoclonal antibodies have all the advantages of human polyclonal antibodies, but none of the disadvantages mentioned above and as such would constitute optimal anti-toxins.

Accordingly, the invention provides human monoclonal antibodies that neutralize *Bacillus anthracis'* Lethal Toxin which are useful in both reducing the risk of a *B. anthracis* infection and for treating an *B anthracis* infected subject. For example, monoclonal antibody IQNPA-1 and IQNPA-2 were identified as antibodies capable of neutralizing *Bacillus anthracis'* Lethal Toxin both in vivo and in vitro.

The IQNPA antibody includes a heavy chain region (SEQ ID NO:2) encoded by the nucleic acid sequence shown below in SEQ ID NO:1, and a light chain (SEQ ID NO:4) encoded by the nucleic acid sequence shown in SEQ ID NO:3 The stop and start codons, defining the coding region are underlined in SEQ ID NO:1 and SEQ ID NO:3.

>IQNPA Hγ nucleotide sequence:
(SEQ ID NO: 1)

```
GGCCCAGCCGGCCATGGACTGGATCTGGAGGATCCTCTTTTTGGTGGCAGCAGCCACAGG
TGCCCACTCCCAGGTCCAGCTTGTGCAGTCTGGGGCTGAGGTGAAGAAGCCTGGGGCCTC
AGTGAAGGTTTCCTGCAAGGCCTCTGGATACACCTTCACTAGCAATGCTATACAATGGGT
GCGCCAGGCCCCCGGACAAAGGCTTGAGTGGGTGGGATGGATCAACGGTGGCGATGGTAA
CACAAAATATTCACAGAAGTTCCAGGGCAGAGTCACCATTAGTAGGGACATATCCGCGAG
CACAGCCTACATGGAGCTGAGCAGCCTGAGATCTGAAGACACGGCTGTGTATTACTGTGC
GAGACATCGTTTGCAAAGAGGGGGGTTCGACCCCTGGGGCCAGGGAACCCTGGTCACCGT
CTCCTCAGCCTCCACCAAGGGCCCATCGGTCTTCCCCCTGGCACCTTCCTCCAAGAGCAC
CTCTGGGGGCACAGCGGCCCTGGGCTGCCTGGTCAAGGACTACTTCCCCGAACCGGTGAC
GGTGTCGTGGAACTCAGGCGCCCTGACCAGCGGCGTGCACACCTTCCCGGCTGTCCTACA
GTCCTCAGGACTCTACTCCCTCAGCAGCGTGGTGACCGTGCCCTCCAGCAGCTTGGGCAC
CCAGACCTACATCTGCAACGTGAATCACAAGCCCAGCAACACCAAGGTGGACAAGAGAGT
TGAGCCCAAATCTTGTGACAAAACTCACACATGCCCACCGTGCCCAGCACCTGAACTCCT
GGGGGGACCGTCAGTCTTCCTCTTCCCCCCAAAACCCAAGGACACCCTCATGATCTCCCG
GACCCCTGAGGTCACATGCGTGGTGGTGGACGTGAGCCACGAAGACCCTGAGGTCAAGTT
CAACTGGTACGTGGACGGCGTGGAGGTGCATAATGCCAAGACAAAGCCGCGGGAGGAGCA
GTACAACAGCACGTACCGTGTGGTCAGCGTCCTCACCGTCCTGCACCAGGACTGGCTGAA
TGGCAAGGAGTACAAGTGCAAGGTCTCCAACAAAGCCCTCCCAGCCCCCATCGAGAAAAC
CATCTCCAAAGCCAAAGGGCAGCCCCGAGAACCACAGGTGTACACCCTGCCCCCATCCCG
GGAGGAGATGACCAAGAACCAGGTCAGCCTGACCTGCCTGGTCAAAGGCTTCTATCCCAG
CGACATCGCCGTGGAGTGGGAGAGCAATGGGCAGCCGGAGAACAACTACAAGACCACGCC
TCCCGTGCTGGACTCCGACGGCTCCTTCTTCCTCTATAGCAAGCTCACCGTGGACAAGAG
CAGGTGGCAGCAGGGGAACGTCTTCTCATGCTCCGTGATGCATGAGGCTCTGCACAACCA
CTACACGCAGAAGAGCCTCTCCCTGTCTCCGGGTAAATGAGGCCTCCGAGGC
```

>IQNPA Hγ amino acid sequence:
(SEQ ID NO: 2)

```
MDWIWRILFLVAAATGAHSQVQLVQSGAEVKKPGASVKVSCKASGYTFTSNAIQWVRQAPGQRLEWVGWINGGDGNT
KYSQKFQGRVTISRDISASTAYMELSSLRSEDTAVYYCARHRLQRGGFDPWGQGTLVTVSSASTKGPSVFPLAPSSK
STSGGTAALGCLVKDYFPEPVTVSWNSGALTSGVHTFPAVLQSSGLYSLSSVVTVPSSSLGTQTYICNVNHKPSNTK
VDKRVEPKSCDKTHTCPPCPAPELLGGPSVFLFPPKPKDTLMISRTPEVTCVVVDVSHEDPEVKFNWYVDGVEVHNA
KTKPREEQYNSTYRVVSVLTVLHQDWLNGKEYKCKVSNKALPAPIEKTISKAKGQPREPQVYTLPPSREEMTKNQVS
LTCLVKGFYPSDIAVEWESNGQPENNYKTTPPVLDSDGSFFLYSKLTVDKSRWQQGNVFSCSVMHEALHNHYTQKSL
SLSPGK
```

>IQNPA Lκ nucleotide sequence:
(SEQ ID NO: 3)

```
GGCCCAGCCGGCCATGGAAGCCCCAGCGCAGCTTCTCTTCCTCCTGCTACTCTGGCTCCC
AGATACCACCGGAGAAATTGTGTTGACGCAGTCTCCAGGCACCCTGTCTTTGTCTCCAGG
GGAAAGAGCCACCCTCTCCTGCAGGGCCAGTCAGAGTGTTAGCTACAGCTCCTTAGCCTG
GTACCAGCAGAAACCTGGCCAGGCTCCCAGCCTCCTCATCTATGGTGCATCCAGCAGGGC
CACTGGCATCCCAGACAGGTTCAGTGGCAGTGGGTCTGGGCCAGACTTCACTCTCACCAT
CAGCAGACTGGAGCCTGAAGATTTTGCAGTTTATTACTGTGTCAGCACTATGGTAACTCACC
GTACACTTTTGGCCAGGGGACCAAGCTGGAGATCAAACGAACTGTGGCTGCACCATCTGT
CTTCATCTTCCCGCCATCTGATGAGCAGTTGAAATCTGGAACTGCCTCTGTTGTGTGCCT
GCTGAATAACTTCTATCCCAGAGAGGCCAAAGTACAGTGGAAGGTGGATAACGCCCTCCA
ATCGGGTAACTCCCAGGAGAGTGTCACAGAGCAGGACAGCAAGGACAGCACCTACAGCCT
CAGCAGCACCCTGACGCTGAGCAAAGCAGACTACGAGAAACACAAAGTCTACGCCTGCGA
AGTCACCCATCAGGGCCTGAGCTCGCCCGTCACAAAGAGCTTCAACAGGGGAGAGTGTTA
GGGCCTCCGAGGC
```

>IQNPA Lκ amino acid sequence:
(SEQ ID NO: 4)

```
MEAPAQLLFLLLLWLPDTTGEIVLTQSPGTLSLSPGERATLSCRASQSVSYSSLAWYQQKPGQAPSLLIYGASSRAT
GIPDRFSGSGSGPDFTLTISRLEPEDFAVYYCQHYGNSPYTFGQGTKLEIKRTVAAPSVFIFPPSDEQLKSGTASVV
CLLNNFYPREAKVQWKVDNALQSGNSQESVTEQDSKDSTYSLSSTLTLSKADYEKHKVYACEVTHQGLSSPVTKSFN
RGEC
```

The IQNLF antibody includes a heavy chain region (SEQ ID NO:6) encoded by the nucleic acid sequence shown below in SEQ ID NO:5, and a light chain (SEQ ID NO:8) encoded by the nucleic acid sequence shown in SEQ ID NO:7 The stop and start codons, defining the coding region are underlined in SEQ ID NO:5 and SEQ ID NO:7.

>IQNLF Hγ nucleotide sequence:
(SEQ ID NO: 5)

```
GGCCCAGCCGGCC ATG GAGTTGGGGCTGTGCTGGCTTTTTCTTGTGGCTATTTTAAAAGG
TGTCCAGTGTGAGGTGCAGCTGTTGGAGTCTGGGGGAGGCTTGGTACAGCCGGGGGGGTC
CCTGAGACTCTCCTGTTCTGGCTCTGGATTCATGTTTAGCAGTTATGCCATGAGCTGGGT
CCGCCAGGCTCCAGGGAAGGGGCTGGAGTGGGTCTCAGGAATTAGTGGTAGCGGTGGTAC
TACAAACTACGCAGACTCCGTGAAGGGCCGGTTCACCATCTCCAGAGACAATTCCAAGAA
CACGCTGTATATGCAAATGAACAGCCTGAGAGCCGAGGACACGGCCGTATATTACTGTGC
GAAAGATGGGGTATATGGCCGACTGGGGGGTTCTGACTACTGGGGCCAGGGAACCCTGGT
CACCGTCTCCTCAGCCTCCACCAAGGGCCCATCAGTCTTCCCCCTGGCACCCTCCTCCAA
GAGCACCTCTGGGGGCACAGCGGCCCTGGGCTGCCTGGTCAAGGACTACTTCCCCGAACC
GGTGACGGTGTCGTGGAACTCAGGCGCCCTGACCAGCGGCGTGCACACCTTCCCGGCTGT
CCTACAGTCCTCAGGACTCTACTCCCTCAGCAGCGTGGTGACCGTGCCCTCCAGCAGCTT
GGGCACCCAGACCTACATCTGCAACGTGAATCACAAGCCCAGCAACACCAAGGTGGACAA
GAAAGTTGAGCCCAAATCTTGTGACAAAACTCACACATGCCCACCGTGCCCAGCACCTGA
ACTCCTGGGGGGACCGTCAGTCTTCCTCTTCCCCCCAAAACCCAAGGACACCCTCATGAT
CTCCCGGACCCCTGAGGTCACATGCGTGGTGGTGGACGTGAGCCACGAAGACCCTGAGGT
CAAGTTCAACTGGTACGTGGACGGCGTGGAGGTGCATAATGCCAAGACAAAGCCGCGGGA
GGAGCAGTACAACAGCACGTACCGTGTGGTCAGCGTCCTCACCGTCCTGCACCAGGACTG
GCTGAATGGCAAGGAGTACAAGTGCAAGGTCTCCAACAAAGCCCTCCCAGCCCCCATCGA
GAAAACCATCTCCAAAGCCAAAGGGCAGCCCCGAGAACCACAGGTGTACACCCTGCCCCC
ATCCCGGGATGAGCTGACCAAGAACCAGGTCAGCCTGACCTGCCTGGTCAAAGGCTTCTA
TCCCAGCGACATCGCCGTGGAGTGGGAGAGCAATGGGCAGCCGGAGAACAACTACAAGAC
CACGCCTCCCGTGCTGGACTCCGACGGCTCCTTCTTCCTCTACAGCAAGCTCACCGTGGA
CAAGAGCAGGTGGCAGCAGGGGAACGTCTTCTCATGCTCCGTGATGCATGAGGGTCTGCA
CAACCACTACACGCAGAAGAGCCTCTCCCTGTCTCCGGGTAAATGAGGCCTCCGAGGC
```

>IQNLF Hγ amino acid sequence:
(SEQ ID NO: 6)

```
MELGLCWLFLVAILKGVQCEVQLLESGGGLVQPGGSLRLSCSGSGFMFSSYAMSWVRQAPGKGLEWVSGISGSGGTT
NYADSVKGRFTISRDNSKNTLYMQMNSLRAEDTAVYYCAKDGVYGRLGGSDYWGQGTLVTVSSASTKGPSVFPLAPS
SKSTSGGTAALGCLVKDYFPEPVTVSWNSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPEVTCVVVDVSHEDPEVKFNWYVDGVEVH
NAKTKPREEQYNSTYRVVSVLTVLHQDWLNGKEYKCKVSNKALPAPIEKTISKAKGQPREPQVYTLPPSRDELTKNQ
VSLTCLVKGFYPSDIAVEWESNGQPENNYKTTPPVLDSDGSFFLYSKLTVDKSRWQQGNVFSCSVMHEGLHNHYTQK
SLSLSPGK
```

>IQNLF Lκ nucleotide sequence:
(SEQ ID NO: 7)

```
GGCCCAGCCGGCCATGTTGCCATCACAACTCATTGGGTTTCTGCTGCTCTGGGTTCCAGC
CTCCAGGGGTGAAATTGTGCTGACTCAGTCTCCAGACTTTCAGTCTGTGAGTCCAAAGGA
GAAAGTCACCATCACCTGCCGGGCCAGCCAGAGCGTTGGTAGTAGCTTACACTGGTACCA
GCAGAAACCAGATCAGTCTCCAAAGCTCCTCATCAAGTATGCTTCCCAGTCCTTCTCAGG
GGTCCCCTCGAGGTTCAGTGGCAGTGGATCTGGGACAGATTTCACCCTCACCATCAATAG
CCTGGAAACTGAAGATGCTGCAACGTATTACTGTCATCAGAGTAGTAGTTTACCTCTCAC
TTTCGGCGGAGGGACCAAGGTGGAGATCAAACGAACTGTGGCTGCACCATCTGTCTTCAT
CTTCCCGCCATCTGATGAGCAGTTGAAATCTGGAACTGCCTCTGTTGTGTGCCTGCTGAA
TAACTTCTATCCCAGAGAGGCCAAAGTACAGTGGAAGGTGGATAACGCCCTCCAATCGGG
TAACTCCCAGGAGAGTGTCACAGAGCAGGACAGCAAGGACAGCACCTACAGCCTCAGCAG
CACCCTGACGCTGAGCAAAGCAGACTACGAGAAACACAAAGTCTACGCCTGCGAAGTCAC
CCATCAGGGCCTGAGCTCGCCCGTCACAAAGAGCTTCAACAGGGGAGAGTGTTAGGGCCT
CCGAGGC
```

>IQNLF Lκ amino acid sequence:
(SEQ ID NO: 8)

```
MLPSQLIGFLLLWVPASRGEIVLTQSPDFQSVSPKEKVTITCRASQSVGSSLHWYQQKPDQSPKLLIKYASQSFSGV
PSRFSGSGSGTDFTLTINSLETEDAATYYCHQSSSLPLTFGGGTKVEIKRTVAAPSVFIFPPSDEQLKSGTASVVCL
LNNFYPREAKVQWKVDNALQSGNSQESVTEQDSKDSTYSLSSTLTLSKADYEKHKVYACEVTHQGLSSPVTKSFNRG
EC
```

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" is meant that the antibody reacts with one or more antigenic determinants of the desired antigen and does not react (i.e., bind) with other polypeptides or binds at much lower affinity ($K_d > 10^{-6}$) with other polypeptides.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

In general, antibody molecules obtained from humans relate to any of the classes IgG, IgM, IgA, IgE and IgD, which differ from one another by the nature of the heavy chain present in the molecule. Certain classes have subclasses as well, such as IgG$_1$, IgG$_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. Antibodies may be raised against N-terminal or C-terminal peptides of a polypeptide. For example, the antibody is raised against lethal factor, edema factor or protective antigen. Optimally, the antibody is raised against domain 4 of a protective antigen peptide. For example, the antibody binds to amino acid residues 608-735 of a protective antigen peptide. The antibody binds to an amino acid sequence of: NNIAVGADES VVKEAHREVI NSSTEGLLLN IDKDIRKILS GYIVEIEDTE GLKEVINDRYDMLNISSLRQ DGKTFID-FKK YNDKLPLYIS NPNYKVNVYA VTKENTIINP SEN-GDTSTNG IKKILIFSKK GYEIG (SEQ ID NO:9) or TNIYTVLDKI KLNAKMNILI RDKRFHYDRN NIAV-GADESV VKEAHREVIN SSTEGLLLNI DKDIRKILSG YIVEIEDTEG LKEVINDRYD MLNISSLRQD GKTFID-FKKY NDKLPLYISNPNYKVNVYAV TKENTIINPS ENGDTSTNGI KKILIFSKKG YEIG (SEQ ID NO:10).

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides are quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to an anthrax epitope when the equilibrium binding constant ($K_d$) is $\leq 1$ μM, preferably $\leq 100$ nM, more preferably $\leq 10$ nM, and most preferably $\leq 100$ pM to about 1 pM, as measured by assays such as radioligand binding assays or similar assays known to those skilled in the art.

As used herein, the term "fragment" when used in reference to a nucleic acid encoding IQNLF or IQNPA is intended to mean a nucleic acid having substantially the same sequence as a portion of a nucleic acid encoding IQNLF or IQNPA The nucleic acid fragment is sufficient in length and sequence to selectively hybridize to an IQNLF or IQNPA antibody encoding nucleic acid or a nucleotide sequence that is complementary to an IQNLF or IQNPA antibody encoding nucleic acid. Therefore, fragment is intended to include primers for sequencing and polymerase chain reaction (PCR) as well as probes for nucleic acid blot or solution hybridization. The meaning of the term is also intended to include regions of nucleotide sequences that do not directly encode IQNLF or IQNPA polypeptides such as the introns, and the untranslated region sequences of the IQNLF or IQNPA encoding gene.

Those skilled in the art will recognize that it is possible to determine, without undue experimentation, if a human monoclonal antibody has the same specificity as a human monoclonal antibody of the invention (e.g., monoclonal antibody IQNPA and IQNLF) by ascertaining whether the former prevents the latter from binding to an anthrax protective antigen polypeptide, lethal factor polypeptide or a anthrax toxin receptor. If the human monoclonal antibody being tested competes with the human monoclonal antibody IQNPA or IQNLF, as shown by a decrease in binding by the human monoclonal antibody IQNPA or IQNLF, then the two monoclonal antibodies bind to the same, or a closely related, epitope. Another way to determine whether a human monoclonal antibody has the specificity of a human monoclonal antibody of the IQNPA or IQNLF is to pre-incubate the human monoclonal antibody of the invention with the protective antigen polypeptide, with which it is normally reactive, and then add the human monoclonal antibody being tested to determine if the human monoclonal antibody being tested is inhibited in its ability to bind the protective antigen polypeptide. If the human monoclonal antibody being tested is inhibited then, in all likelihood, it has the same, or functionally equivalent, epitopic specificity as the monoclonal antibody of the invention. Screening of human monoclonal antibodies of the invention, is also carried out by utilizing B. anthracis and determining whether the test monoclonal antibody is able to neutralize B. anthracis.

Various procedures known within the art are used for the production of the monoclonal antibodies directed against a protein of anthrax, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Also included in the invention are functional fragments of IQNLF and IQNPA antibodies. By functional fragment is meant an antibody molecule or fragment thereof having substantially the same heavy and light chain CDR amino acid sequences as found in IQNLF or IQNPA. The functional fragment which still retains some of all or LF or PA binding activity. Such functional fragments can include, for example, antibody functional fragments such as Fab, F(ab)$_2$, Fv, single chain Fv (scFv). Other functional fragments can include, for example, heavy or light chain polypeptides, variable region polypeptides or CDR polypeptides or portions thereof so long as such functional fragments retain binding activity, specificity, LF or PA binding activity or neutralizing activity. The term is also intended to include polypeptides encompassing, for example, modified forms of naturally occurring amino acids such as D-stereoisomers, non-naturally occurring amino acids, amino acid analogues and mimetics so long as such polypeptides retain functional activity as defined above. When used in reference to a functional fragment, not all IQNLF or IQNPA CDRs need to be represented. Rather, only those CDRs that would normally be present in the antibody portion that corresponds to the functional fragment. Similarly, the term "functional fragment when used in reference to an encoding nucleic acid is intended to refer to a nucleic acid encoding a antibody or functional fragment being absent of the substitution of IQNLF or IQNPA amino acids outside of the CDRs and having substantially the same nucleotide sequence as the heavy and light chain CDR nucleotide sequences and encoding substantially the same CDR amino acid sequences as found in IQNLF or IQNPA The meaning functional fragment is intended to include minor variations and modifications of the antibody so long as its function remains uncompromised. Such functional fragments are well known to those skilled in the art. Such terms are described in, for example, Harlow and Lane, Antibodies: A Laboratory Manual, Cold Spring Harbor Laboratory, New York (1989); Molec. Biology and Biotechnology: A Comprehensive Desk Reference (Myers, R. A. (ed.), New York: VCH Publisher, Inc.); Huston et al., Cell Biophysics, 22:189-224 (1993); Pluckthun and Skerra, Meth. Enzymol., 178:497-515 (1989) and in Day, E. D., Advanced Immunochemistry, Second Ed., Wiley-Liss, Inc., New York, N.Y. (1990).

In the case where there are two or more definitions of a term which is used and/or accepted within the art, the definition of the term as used herein is intended to include all such meanings unless explicitly stated to the contrary. A specific example is the use of the term "CDR" to describe the non-contiguous antigen combining sites found within the variable region of both heavy and light chain polypeptides. This particular region has been described by Kabat et al., supra, and by Chothia et al., J. Mol. Biol. 196:901-917 (1987) and by MacCallum et al., J. Mol. Biol. 262:732-745 (1996) where the definitions include overlapping or subsets of amino acid residues when compared against each other. Nevertheless, application of either definition to refer to a CDR of IQNLF or IQNPA or variants thereof is intended to be within the scope of the term as defined and used herein. The amino acid residues which encompass the CDRs as defined by each of the above cited references are set forth below in Table A as a comparison.

TABLE A

CDR Definitions

|  |  | Kabat[1] | Chothia[2] | MacCallum[3] |
|---|---|---|---|---|
| $V_H$ | CDR1 | 31-35 | 26-32 | 30-35 |
| $V_H$ | CDR2 | 50-65 | 53-55 | 47-58 |
| $V_H$ | CDR3 | 95-102 | 96-101 | 93-101 |
| $V_L$ | CDR1 | 24-34 | 26-32 | 30-36 |
| $V_L$ | CDR2 | 50-56 | 50-52 | 46-55 |
| $V_L$ | CDR3 | 89-97 | 91-96 | 89-96 |

[1]Residue numbering follows the nomenclature of Kabat et al., supra
[2]Residue numbering follows the nomenclature of Clothia et al., supra
[3]Residue numbering follows the nomenclature of MacCallum et al., supra Sequences corresponding to the IQNPA CDRs include, for example, those regions defined by Kabat et al., supra, and/or those regions defined by Chothia et al., supra, as well as those defined by MacCallum et al., supra. The IQNPA CDR fragments for each of the above definitions correspond to the nucleotides set forth below in Table B when numbered in accordance to SEQ ID NO: 1 and 3. The nucleotide sequence numbering is taken from the primary sequence shown in SEQ ID NOS:1 and 3 and conforms to the definitions previously set forth in Table A.

TABLE B

IQNPA CDR Nucleotide Residues

|  |  | Kabat | Chothia | MacCallum |
|---|---|---|---|---|
| $V_H$ | CDR1 | 104-118 | 89-109 | 101-118 |
| $V_H$ | CDR2 | 161-211 | 170-181 | 152-190 |
| $V_H$ | CDR3 | 308-331 | 311-328 | 302-328 |
| $V_L$ | CDR1 | 83-115 | 89-109 | 101-121 |
| $V_L$ | CDR2 | 161-181 | 161-169 | 149-178 |
| $V_L$ | CDR3 | 278-304 | 284-301 | 278-301 |

Similarly, the IQNPA CDR fragments for each of the above definitions correspond to the amino acid residues set forth below in Table C, when numbered in accordance to SEQ ID NO:2 and 4. The amino acid residue number is taken from the primary sequence shown in SEQ ID NOS:2 and 4 and conforms to the definitions previously set forth in Table A.

TABLE C

IQNPA CDR Amino Acid Residues

|  |  | Kabat | Chothia | MacCallum |
|---|---|---|---|---|
| $V_H$ | CDR1 | Lys31-Ala35 | Ser26-Lys32 | Val30-Ala35 |
| $V_H$ | CDR2 | Ser50-Trp66 | Ile53-Val56 | Thr47-Ala59 |
| $V_H$ | CDR3 | Tyr99-Arg106 | Met100-Leu105 | Thr97-Leu105 |
| $V_L$ | CDR1 | Leu24-Ser34 | Gln26-Ser32 | Thr30-Gly36 |
| $V_L$ | CDR2 | Ser50-Trp56 | Ser50-Ser52 | Ser46-Ala55 |
| $V_L$ | CDR3 | Gly89-Ser97 | Asp91-Ile96 | Gly89-Ile96 |

Thus, the invention also provides nucleic acid fragments encoding substantially the same amino acid sequence as a CDR of a IQNLF heavy or light chain polypeptide.

Sequences corresponding to the IQNLF CDRs include, for example, those regions defined by Kabat et al., supra, and/or those regions defined by Chothia et al., supra, as well as those defined by MacCallum et al., supra. The IQNLF CDR fragments for each of the above definitions correspond to the nucleotides set forth below in Table D when numbered in accordance to SEQ ID NO: 5 and 7. The nucleotide sequence numbering is taken from the primary sequence shown in SEQ ID NOS:5 and 7 and conforms to the definitions previously set forth in Table A.

TABLE D

IQNLF CDR Nucleotide Residues

| | | Kabat | Chothia | MacCallum |
|---|---|---|---|---|
| $V_H$ | CDR1 | Lys31-Ala35 | Ser26-Lys32 | Val30-Ala35 |
| $V_H$ | CDR2 | Ser50-Trp66 | Ile53-Val56 | Thr47-Ala59 |
| $V_H$ | CDR3 | Tyr99-Arg106 | Met100-Leu105 | Thr97-Leu105 |
| $V_L$ | CDR1 | Leu24-Ser34 | Gln26-Ser32 | Thr30-Gly36 |
| $V_L$ | CDR2 | Ser50-Trp56 | Ser50-Ser52 | Ser46-Ala55 |
| $V_L$ | CDR3 | Gly89-Ser97 | Asp91-Ile96 | Gly89-Ile96 |

Similarly, the IQNLF CDR fragments for each of the above definitions correspond to the amino acid residues set forth below in Table D, when numbered in accordance to SEQ ID NO: 6 and 8. The amino acid residue number is taken from the primary sequence shown in SEQ ID NOS:6 and 8 and conforms to the definitions previously set forth in Table A.

TABLE E

IQNPA CDR Amino Acid Residues

| | | Kabat | Chothia | MacCallum |
|---|---|---|---|---|
| $V_H$ | CDR1 | Val31-Gly35 | Ser26-Gln32 | Leu30-Gly35 |
| $V_H$ | CDR2 | Ser50-Trp66 | Met53-Val56 | Met47-Ala59 |
| $V_H$ | CDR3 | Tyr99-Arg106 | Met100-Leu105 | Thr97-Leu105 |
| $V_L$ | CDR1 | Thr24-Pro34 | Ser26-Val32 | Gln30-Glu36 |
| $V_L$ | CDR2 | Ser50-Gln56 | Ser50-Leu52 | Gln46-Tyr55 |
| $V_L$ | CDR3 | Asp89-Thr97 | Thr91-Ser96 | Asp89-Ser96 |

Thus, the invention also provides nucleic acid fragments encoding substantially the same amino acid sequence as a CDR of a IQNPA heavy or light chain polypeptide.

As used herein, the term "substantially" or "substantially the same" when used in reference to a nucleotide or amino acid sequence is intended to mean that the nucleotide or amino acid sequence shows a considerable degree, amount or extent of sequence identity when compared to a reference sequence. Such considerable degree, amount or extent of sequence identity is further considered to be significant and meaningful and therefore exhibit characteristics which are definitively recognizable or known. Thus, a nucleotide sequence which is substantially the same nucleotide sequence as a heavy or light chain of IQNLF or IQNPA and fragments thereof, refers to a sequence which exhibits characteristics that are definitively known or recognizable as encoding or as being the amino acid sequence of IQNLF or IQNPA. Minor modifications thereof are included so long as they are recognizable as a IQNLF or IQNPA antibody sequence. Similarly, an amino acid sequence which is substantially the same amino acid sequence as a heavy or light chain of IQNLF or IQNPA or functional fragment thereof, refers to a sequence which exhibits characteristics that are definitively known or recognizable as representing the amino acid sequence of IQNLF or IQNPA and minor modifications thereof.

In addition to conservative substitutions of amino acids, minor modifications of the IQNLF or IQNPA encoding nucleotide sequences which allow for the functional replacement of amino acids are also intended to be included within the definition of the term. The substitution of functionally equivalent amino acids encoded by the IQNLF or IQNPA nucleotide sequences is routine and can be accomplished by methods known to those skilled in the art. Briefly, the substitution of functionally equivalent amino acids can be made by identifying the amino acids which are desired to be changed, incorporating the changes into the encoding nucleic acid and then determining the function of the recombinantly expressed and modified IQNLF or IQNPA polypeptide or polypeptides. Rapid methods for making and screening multiple simultaneous changes are well known within the art and can be used to produce a library of encoding nucleic acids which contain all possible or all desired changes and then expressing and screening the library for IQNLF or IQNPA polypeptides which retain function. Such methods include, for example, codon based mutagenesis, random oligonucleotide synthesis and partially degenerate oligonucleotide synthesis.

Identification of amino acids to be changed can be accomplished by those skilled in the art using current information available regarding the structure and function of antibodies as well as available and current information encompassing methods for CDR grafting procedures. For example, CDRs can be identified within the donor antibody by any or all of the criteria specified in Kabat et al., supra, Chothia et al., supra, and/or MacCallum et al., supra, and any or all non-identical amino acid residues falling outside of these CDR sequences can be changed to functionally equivalent amino acids. Using the above described methods known within the art, any or all of the non-identical amino acids can be changed either alone or in combination with amino acids at different positions to incorporate the desired number of amino acid substitutions at each of the desired positions. The IQNLF or IQNPA polypeptides containing the desired substituted amino acids are then produced and screened for retention or augmentation of function compared to the unsubstituted IQNLF or IQNPA polypeptides. Production of the substituted IQNLF or IQNPA polypeptides can be accomplished by, for example, recombinant expression using methods known to those skilled in the art. Those IQNLF or IQNPA polypeptides which exhibit retention or augmentation of function compared to unsubstituted IQNLF or IQNPA are considered to contain minor modifications of the encoding nucleotide sequence which result in the functional replacement of one or more amino acids.

The functional replacement of amino acids is beneficial since it allows for the rapid identification of equivalent amino acid residues without the need for structural information or the laborious procedures necessary to assess and identify which amino acid residues should be considered for substitution in order to successfully transfer binding function from the donor. Moreover, it eliminates the actual step-wise procedures to change and test the amino acids identified for substitution. Essentially, using the functional replacement approach described above, all non-identical amino acid residues between the donor and the human framework can be identified and substituted with any or all other possible amino acid residues at each non-identical position to produce a population of substituted polypeptides containing all possible or all desired permutations and combinations. The population of substituted polypeptides can then be screened for those substituted polypeptides which retain function. Using the codon based mutagenesis procedures described above, the generation of a library of substituted amino acid residues and the screening of functionally replaced residues has been used for the rapid production of grafted therapeutic antibodies as well as for the rapid alteration of antibody affinity. Such procedures are exemplified in, for example, Rosok et al., J. Biol. Chem. 271:22611-22618 (1996) and in Glaser et al., J. Immunol. 149:3903-3913 (1992), respectively Antibodies are purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

It is desirable to modify the antibody of the invention with respect to effector function, so as to enhance, e.g., the effectiveness of the antibody in treating *B. anthracis*. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling is accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding is achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6[3-(2-pyridyldithio) propionamido]hexanoate (Pierce Chem. Co., Cat #21651G); (iv) Sulfo-LC-SPDP (sulfosuccinimidyl 6[3-(2-pyridyldithio)-propianamide] hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

Methods of Treatment

The invention provides for both prophylactic, post-exposure prophylactic and therapeutic methods of treating a subject at risk of (or susceptible to) a *Bacillus anthracis* infection. Passive immunization has proven to be an effective and safe strategy for the prevention and treatment of infectious diseases. Passive immunization using a neutralizing human monoclonal antibody provides an immediate treatment strategy for emergency prophylaxis and treatment of *Bacillus anthracis* infection. In addition, passive immunization in a subject exposed to anthrax using a neutralizing human monoclonal antibody enables the subject to mount an endogenous protective response against the infecting agent, thereby rendering active immunization with an anthrax vaccine for future protection unnecessary. The infecting agent, in all its immunogenic and non-immunogenic components, will be processed and presented to the specific immune system, giving rise to long-term protective immunity.

By binding to the *Bacillus anthracis* the IQNPA and IQNLF antibodies modulate the recognition of the antigen by a subject immune system, thus inducing the subjects natural immunity.

A *Bacillus anthracis* infection is prevented or the risk of developing a *Bacillus anthracis* infection is reduced in a subject by administering to the subject an IQNPA or IQNLF antibody. A subject at risk for *Bacillus anthracis* infection includes individuals who have been, or suspected of having been, or may come into contact (i.e., exposed) with spores or vegetative of a cells *Bacillus anthracis* strain in any way. For example, this may be by becoming exposed to a deliberately or undeliberately disseminated cloud of anthrax spores, by touching infected soil, animals, animal products or by working with spores or vegetative cells in a laboratory. Administration of a prophylactic agent occurs prior to the manifestation of symptoms characteristic of the *Bacillus anthracis* such that a disease or disorder is prevented or, alternatively, delayed in its progression or severity.

Alternatively, the IQNPA or IQNLF antibodies are administered therapeutically. For example, the IQN antibodies are administered to a subject after the manifestation of a symptom of a *Bacillus anthracis* infection. Optionally, the IQN antibodies are administered with an antibiotic treatment regime. Treatment reduces the severity or alleviates a symptom of a *Bacillus anthracis* infection Efficaciousness of treatment is determined in association with any known method for diagnosing or treating a *Bacillus anthracis* infection. Alleviation of one or more symptoms of the *Bacillus anthracis* infection indicates that the compound confers a clinical benefit.

Symptoms of *Bacillus anthracis* vary depending on how the disease was contracted (e.g., cutaneous, inhalation or intestinal), but symptoms usually occur within 7 days. Most (about 95%) anthrax infections occur when the bacterium enters a cut or abrasion on the skin, such as when handling contaminated wool, hides, leather or hair products (especially goat hair) of infected animals. Skin infection begins as a raised itchy bump that resembles an insect bite but within 1-2 days develops into a vesicle and then a painless ulcer, usually 1-3 cm in diameter, with a characteristic black necrotic (dying) area in the center. Lymph glands in the adjacent area may swell. About 20% of untreated cases of cutaneous anthrax will result in death. Initial symptom of inhalation anthrax may resemble a common cold. After several days, the symptoms may progress to severe breathing problems and shock. Inhalation anthrax is usually fatal. The intestinal disease form of anthrax may follow the consumption of contaminated meat and is characterized by an acute inflammation of the intestinal tract. Initial signs of nausea, loss of appetite, vomiting, fever are followed by abdominal pain, vomiting of blood, and severe diarrhea. Intestinal anthrax results in death in 25% to 60% of cases.

*Bacillus anthracis* infection is diagnosed by isolating *B. anthracis* from the blood, skin lesions, or respiratory secretions or by measuring specific antibodies in the blood of persons with suspected cases.

The IQNPA or IPNLF antibodies are administered before exposure to a *Bacillus anthracis*. For example, the monoclonal antibody is administered at least 1 year before *Bacillus anthracis* exposure. For example, the monoclonal antibody is administered 1-7 days, 1 week, 2 weeks, 3 weeks, 1 month, 2 months, 3 months or more before exposure to *Bacillus anthracis*. Alternatively, the monoclonal antibody is administered after exposure to *Bacillus anthracis*. For example, the monoclonal antibody is administered at least 1 hour, 2 hours, 3 hours, 4 hours, 8 hours or more after *Bacillus anthracis* exposure. The monoclonal antibody is administered 1 day, 2 days, 3 days, 4 days or more after exposure to *Bacillus anthracis*. The IPNPA or IPNLF antibodies are administered as a single dose. Alternatively, the IQNPA or IPNLF antibodies are administered in multiple doses. For example, the IQNPA or IPNLF antibodies are administered in two, three, four or five doses. The doses are for example,1, 2, 3, 4 or more days apart.

Optionally, the IQNPA or IPNLF antibodies are co-administered with an antibiotic. Alternatively the IQNPA or IPNLF antibodies are administered prior to or after administration of an antibiotic. Antibiotics include for example ciprofloxacin, doxycycline, amoxicillin, and penicillin G procaine.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Drug Compositions

Therapeutic or prophylactic compositions are provided herein, which generally comprise mixtures of one or more IQNPA or IPNLF monoclonal antibodies and combinations thereof. The prophylactic compositions are used to prevent *Bacillus anthracis* infection and the therapeutic compositions are used to treat individuals following *Bacillus anthracis* infection. Prophylactic uses include the provision of increased antibody titer to *Bacillus anthracis* in a treated subject. In this manner, subjects at high risk of contracting *Bacillus anthracis* are provided with passive immunity to *Bacillus anthracis*.

Optionally, the composition is administered in conjunction with ancillary immunoregulatory agents. For example, cytokines, lymphokines, and chemokines, including, but not limited to, IL-2, modified IL-2 (Cys125→Ser125), GM-CSF, IL-12, γ-interferon, IP-10, MIP1β, and RANTES.

The antibodies or agents of the invention (also referred to herein as "active compounds"), and derivatives, fragments, analogs and homologs thereof, are incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, kit, or dispenser together with instructions for administration.

Screening for *Bacillus anthracis* Bacterium

Antibodies directed against a *Bacillus anthracis* are useful in methods known within the art relating to the localization and/or quantitation of a *Bacillus anthracis* bacterium in a sample. A *Bacillus anthracis* bacterium is detected in a sample by contacting a sample known to or suspected of containing the bacterium with an IQPN antibody and detecting the presence or absence of a antibody-bacterium complex. The presence of a complex indicates that the sample contains *Bacillus anthracis*. Conversley the absence of a complex indicates that the sample does not contain *Bacillus anthracis*. The sample is contacted with the IQN antibody in vitro. Alternatively, the sample is contacted with the IQN antibody in vivo.

An IQN antibody is used to isolate, i.e., detect, a *Bacillus anthracis* bacterium in a sample by standard techniques, such as immunoaffinity, chromatography or immunoprecipitation. An IQN antibody is also used diagnostically to monitor protein levels in tissue as part of a clinical testing procedure, e.g., to, for example, determine the efficacy of a given treatment regimen. Detection can be facilitated by coupling (i.e., physically linking) the antibody to a detectable label. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of detectable subtances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H. Indirect labeling includes detection of a primary antibody using a fluorescently-labeled secondary antibody and end-labeling of a DNA probe with biotin such that it can be detected with fluorescently-labeled streptavidin.

The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph, skin lesion, respiratory secretions, vesicular fluid or cerebrospinal fluid.

Also included in the invention is a kit for detecting the presence of Bacillus anthracis bacterium in a sample. For example, the kit can comprise: a labeled compound or agent capable of detecting Bacillus anthracis (e.g., IQNPA-1, IQNPA-2, IQNLF-1 or IQNLF-2) in a sample; means for determining the amount of Bacillus anthracis in the sample; and means for comparing the amount of Bacillus anthracis in the sample with a standard. The compound or agent is packaged in a suitable container. The kit further comprise instructions for using the kit to detect Bacillus anthracis bacterium in a sample.

The invention will be further illustrated in the following non-limiting examples.

EXAMPLE 1

Preparation of Human Monoclonal Antibodies against Anthrax

The following general methods were used to prepare the human monoclonal antibodies of the invention.

Reagents

Culture medium DMEM/HAM's F12 (Cambrex Biosciences 12-719F) is prepared with 1300 mg/l sodium bicarbonate (Merck), 55 mg/l sodium pyruvate (Fluka), 2.3 mg/l 2-mercaptoethanol (Merck). 60 mg/L Gentamycin (Sigma), and 8% Fetal Bovine Serum (Wisent). In fusion experiments, the medium is further supplemented with 13.61 mg/l hypoxanthine (Fluka) and 3.83 mg/l thymidine (Fluka). This medium is referred to as DMEM/HAM's F12/HT.

Selection of hybridomas is performed in DMEM/HAM's F12/HT supplemented with 1% of IL-6 containing supernatant of a human bladder carcinoma cell line T24 (T24CM) and 0.4 M aminopterin (Sigma). Fusion medium: Ready to use hypo-osmotic buffer (eppendorf)

Cell Cultures

Mutant EL-4 thymoma cells, EL-4/B5 are routinely cultured in DMEM/HAM's F12 supplemented with 8% FCS) between cell concentrations of $1\times10^4$ to $1\times10^6$ c/ml. If cells overgrow $1\times10^6$ c/ml, they may lose their B-cell stimulating activity. Murine myeloma cells NS-1, or xenohybrids K6H6B5 and PAI-1 were used as fusion partners for murine and human B-cells respectively. Cells are routinely cultured in DMEM/HAM's F12/HT supplemented with 10% FCS in concentrations between $5\times10^4$ and $15\times10^5$ cells per ml. One day before fusion, cultures were split 1:3 to create a log-phase culture at the day of fusion.

Preparation of Human T-Cell/Macrophage Supernatant (TSN)

Freshly isolated mononuclear cells were centrifuged for 10 minutes at 2000 N/kg. Subsequently, B- and T-cells were separated according to a modification of the method described by Gutierrez et al. (1979). The pellet was resuspended in 5 ml 100% SIP. Then, a 10 ml layer of 70% SIP followed by a 25 ml layer of 50% SIP were layered onto the 100% SIP. The gradient was centrifuged for 10 min. at 25,000 N/kg. The enriched T-cell fraction remaining at the interface between 70% and 50% SIP is collected and washed twice with DMEM/HAM's F12 supplemented with 10% FCS. Washed cells are stimulated for 40-45 h in DMEM/HAM's F12 supplemented with 10% FCS, 5 g/ml PHA (Wellcome) and 10 ng/ml PMA (Sigma). Finally, supernatant is harvested, filtered through a 0.2 m membrane filter and stored in aliquots at −70° C.

EL-4/B-Cell Cultures

EL-4/B-cell cultures are prepared as described by Zubler et al. Briefly, crude or purified B-cells are mixed with TSN and 50,000 irradiated (2500 RAD) EL-4/B5-cells in a final volume of 2001 DMEM/HAM's F12 supplemented with 10% FCS in 96-well flat bottomed tissue culture plates. The optimal amount of TSN is established for each batch by titration. Usually 10% TSN was sufficient for optimal stimulation of human B-cells whereas 20% TSN is usually required for murine B-cells. The cultures are incubated at 37° C., with 5% CO2 and 100% humidity. Between Day 8 and Day 12, supernatants are tested for immunoglobulin production.

Isolation of Mononuclear Cells

Blood was drawn from an Anthrax vaccinee, 5-10 days after the latest booster injection. The blood was diluted 50/50 v/v with sterile PBS and spun down on Isopaque Ficoll (45 min. 400 g). The mononuclear cells resulting from this procedure were either used fresh, or frozen into liquid $N_2$.

Enrichment of Human B-Cells

The isolated mononuclear cells (fresh or thawed) were enriched for B lymphocytes with 'untouched B cell' protocol of an AutoMACS apparatus (Miltenyi Biotec Inc. Auburn, Calif.). These enriched B cell suspension were used either fresh or thawed from liquid $N_2$.

CD40 Expansion of Lymphocytes

Enriched B-lymphocytes are expanded using 3T6CD40L expansion system. Briefly, 3TCD40L cells were harvested at ~80% confluence. The culture medium was discarded and EDTA buffer was added ( 6 ml in T75 or 3 ml in T25). The cells were resuspended and irradiated with 100 Gy with a Cs137 source. The cell are washed in linolea medium and counted. The required concentration in 24 wells: 8×10e4 ml; in 96 wells: 2×10e5/ml. A similar amount and volume B cells are added to the to radiated 3T6CD40L cells (i.e., 1:1). 10 ng/ml rhIL-4 was added to the culture.

The culture medium was refreshed,-half of the medium+IL-4 every 3 days. Every 7 days freshly radiated 3T6CD40L cells ($2\times10^5$ in 24 wells; 5×10e3 in 96 wells) were added or B cells were harvested and transferred to new plate with freshly radiated 3T6CD40L (same concentration as start culture). After ~5 to 7 days characteristic B cell clumps were visible in culture. Cultured B cells were harvested between days 5 and 11 by carefully resuspending cells with a Pasteur pipette.

Panning Procedure

Six-well culture plates were incubated overnight with 4 ml per well of a solution containing 1 to 10 ug antigen in 0.05 M sodiumcarbonate buffer pH=9.6. Subsequently, the wells were washed with PBS and directly used for panning experiments or stored at −20° C. Panning was performed by incubating enriched B-cells on antigen coated wells for 1 to 2 hour at 37° C., 5% $CO_2$ and 100% humidity. After this incubation, the unattached cells were removed gently by three subsequent washes with PBS. Then, the antigen-bound, specific B-cells were recovered by incubating each well with 250 ul PBS containing 1.1 mM Na2EDTA and 0.05% trypsin (Flow, cat no. 16-893-49) pH=7.5 for 2 minutes. Trypsin treatment was stopped by addition of 5 ml DMEM/HAM's F12 supplemented with 10% FCS. Finally, the entire surface of the wells was flushed with the medium using a pasteur pipette in order to remove residual attached B-cells mechanically.

Electrofusion

Electrofusion of lymphocyts to K6H6/B5 myeloma cells occurs in a ratio's ranging from 1:0.5 to 1:10 in 60 μL of fusion medium in a micro chamber. B-cell cultures were mixed myeloma cells in 2-ml centrifuge tubes. The cells were rendered serum-free by washing once with fusion medium. Then, the cell suspension was centrifuged and the pellet was resuspended in 60 μL fusion medium at room temperature. The complete cell suspension was pipetted into the internal space of a fusion chamber. This chamber consists of two stainless steel, disc-shaped electrodes embedded in a perspex box. The electrodes are separated by a teflon spacer of varying diameter and 0.50 mm thickness. Alignment occurs by an alternating electric field of 1 MHz and 150 V/cm for 30 s, immediately followed by a peek pulse of 1500 V/cm for 15 μs Then, immediately a square, high field pulse of 3 kV/cm and 10 s duration was applied causing cell membrane breakdown. The alternating field was applied again for 30 s in order to allow intermingling of cells and resealing of membranes. The contents of the fusion chamber were transferred to 20 ml selection medium (HAT) and plated into a 96-well microculture plate. At Day 9, the cultures were examined for hybridoma growth and the supernatants were tested for immunoglobulin production.

PEG Fusion:

PEG fusion to K6H6/B5 myeloma cells occurs in a 1:1 ratio in 1-1.5 ml PEG 4000 (50%) solution for 3 minutes. After two washing steps (step one with DMEM/F12 and step two with HT-medium), these fusion products were seeded into microtiter plates and cultured in selection medium (HAT) for 9 days.

Monoclonal antibodies specific for *B. anthracis* were screened by methods known in the art.

EXAMPLE 2

In Vitro Evaluation of the Neutralization Activity of Human Monoclonal Antibodies against Anthrax The ability hMabs IQNPA-1 and IQNPA-2 to neutralize anthrax toxin in vitro was determined. Target cells were exposed to *B. Anthracis* protective antigen (PA) that had been pre-incubated with hMabs IQNPA-1 and IQNPA-2 (pre-exposure). Alternatively, target cells were incubated with PA prior to in exposure to hMabs IQNPA-1 and IQNPA-2 (post-exposure)

Pre-exposure

Figure 2:
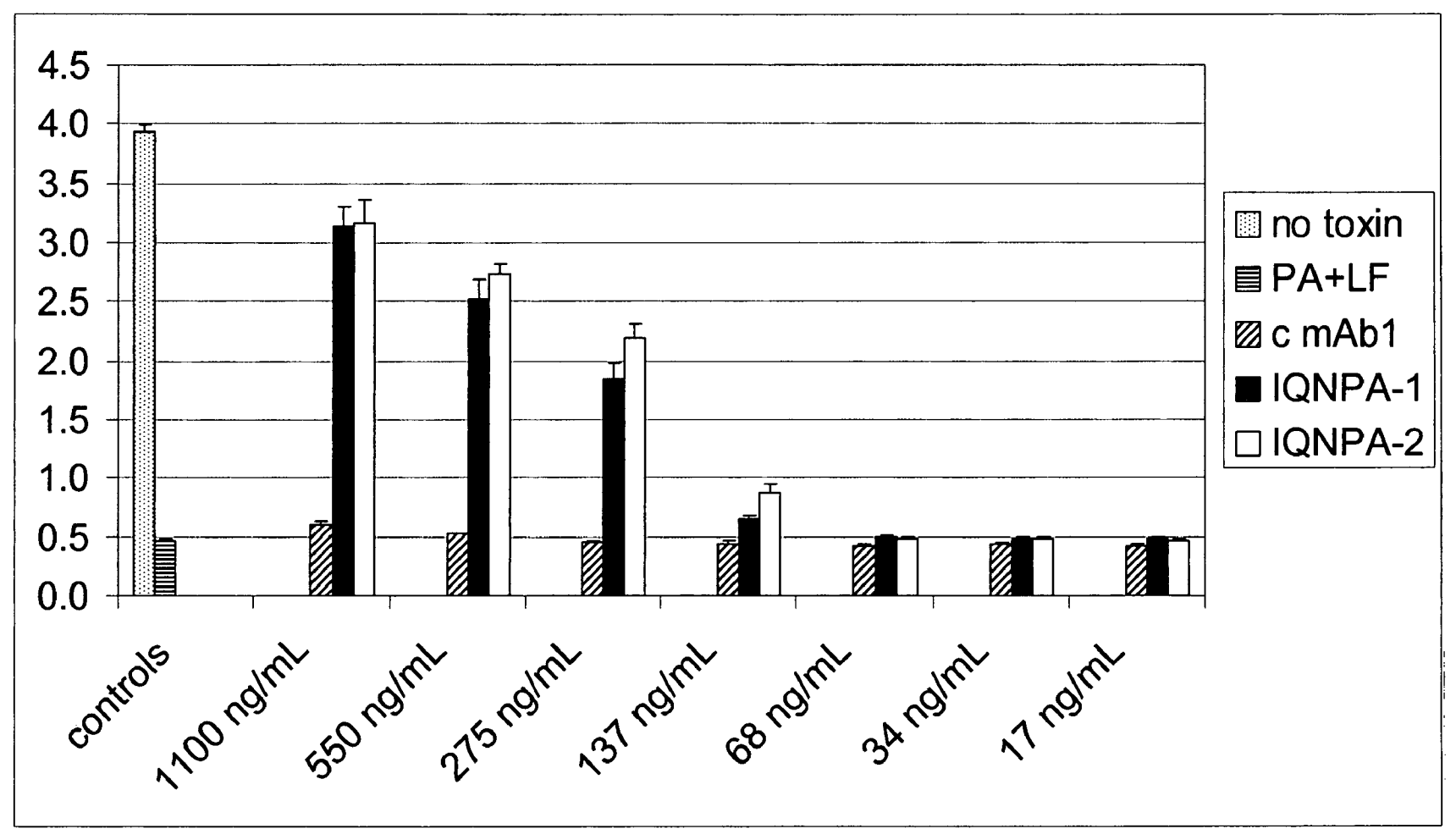

Briefly, 50,000 RAW cells/well were plated (target cells). PA and hMab were pre-incubated for 1 hr and then added to RAW cell culture. Lethal factor (LF) was added and the culture was incubated for 12 to 15 hrs at 37° C. WST-1 was added and OD450 was measured at 1 and 2 hrs. This experiment was repeated twice. Results are shown in FIGS. 1 and 2.

Post-exposure

Figure 3:
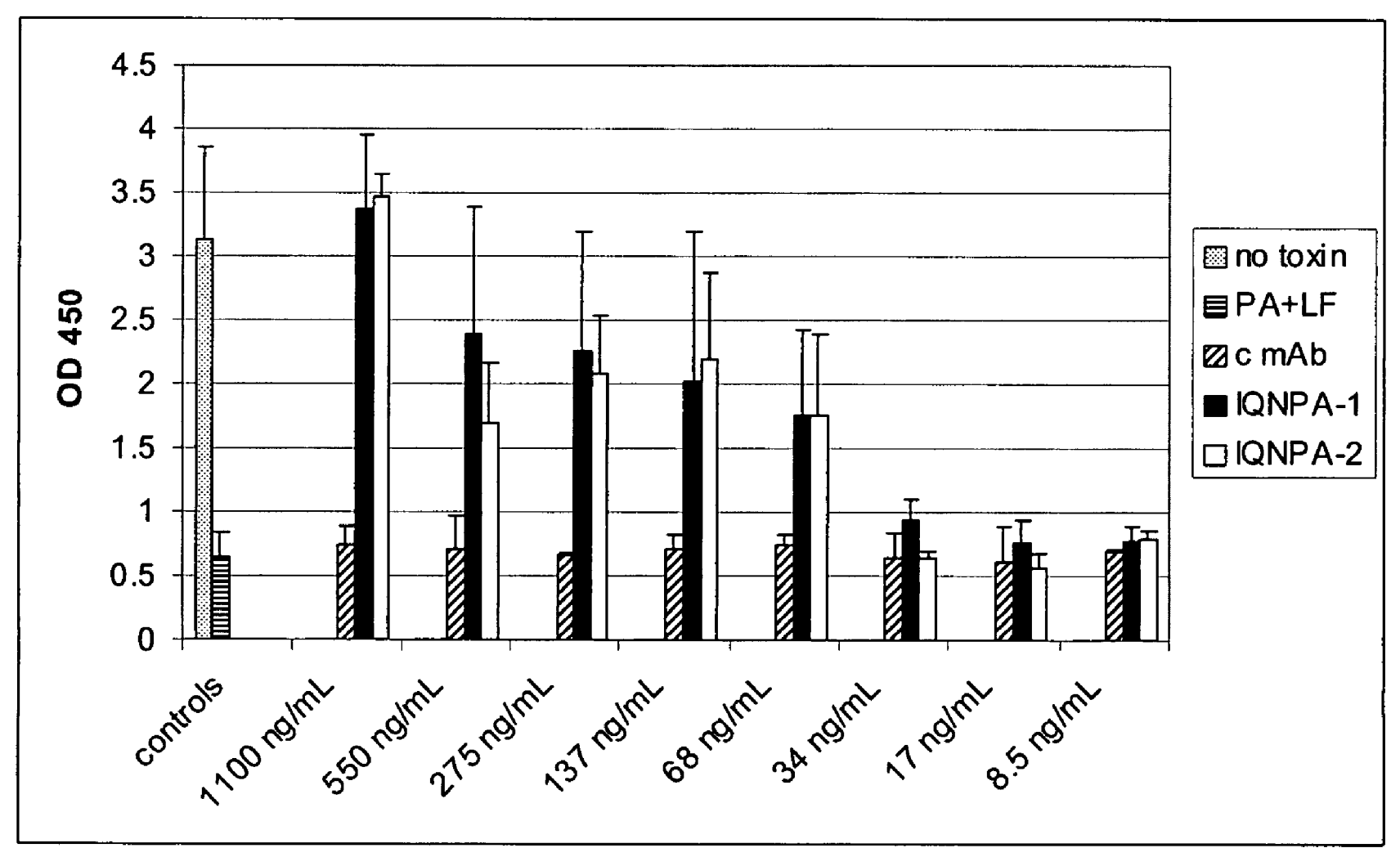
Figure 4:
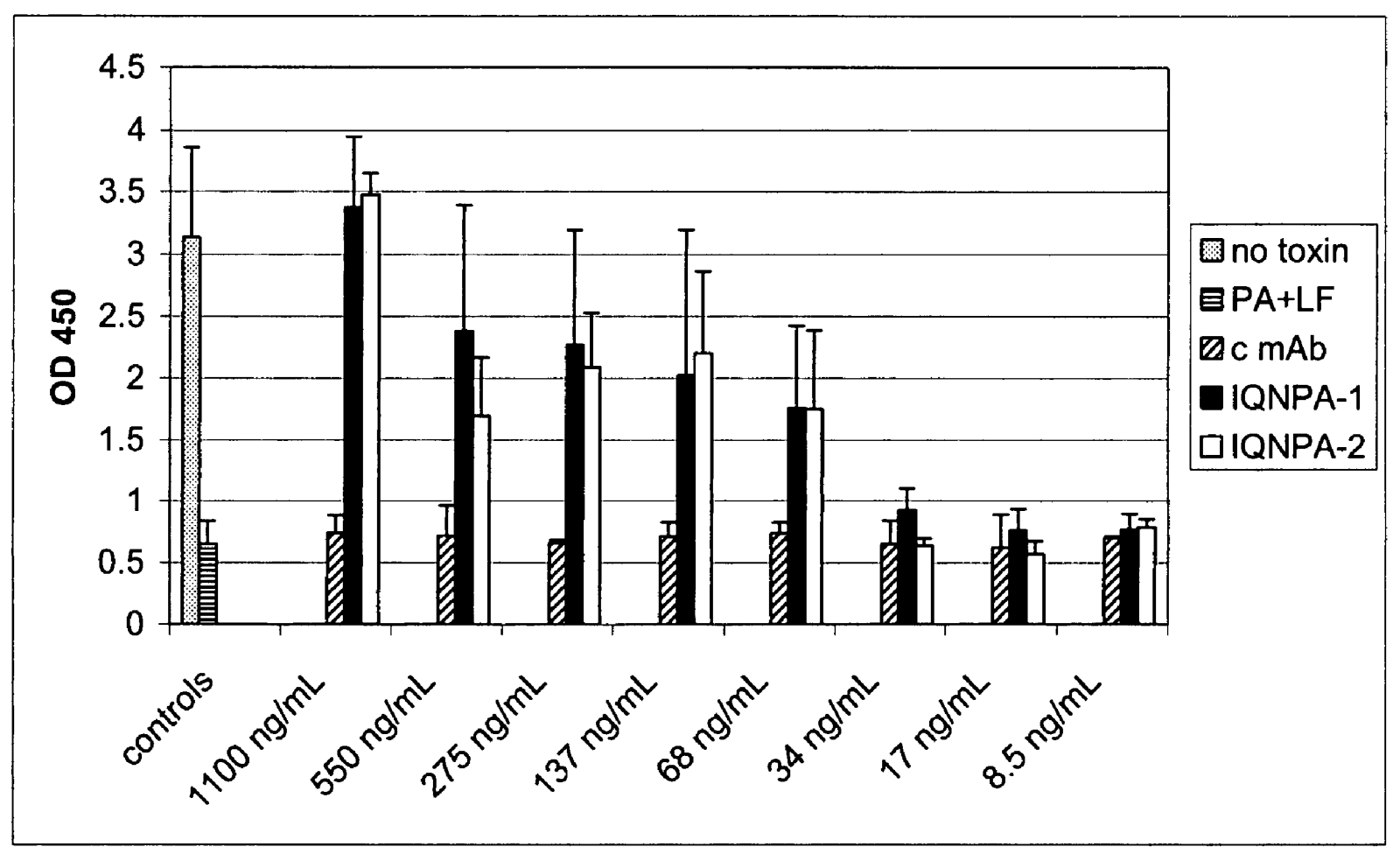

RAW264.7 cells (target cells) were incubated with PA for either 2 hours or three hours prior to addition of hMabs IQNPA-1 or IQNPA-2. LF and IQNPA-1 or IQNPA-2 was added and the culture was incubated for 12 to 15 hrs at 37° C. WST-1 was added and OD450 was measured at 1 and 2 hrs. This experiment was repeated twice. As shown in FIGS. 3-4, hMabs IQNPA-1 and IQNPA-2 are able to fully neutralize lethal toxin after protective antigen had bound to the target cells.

Figure 5:
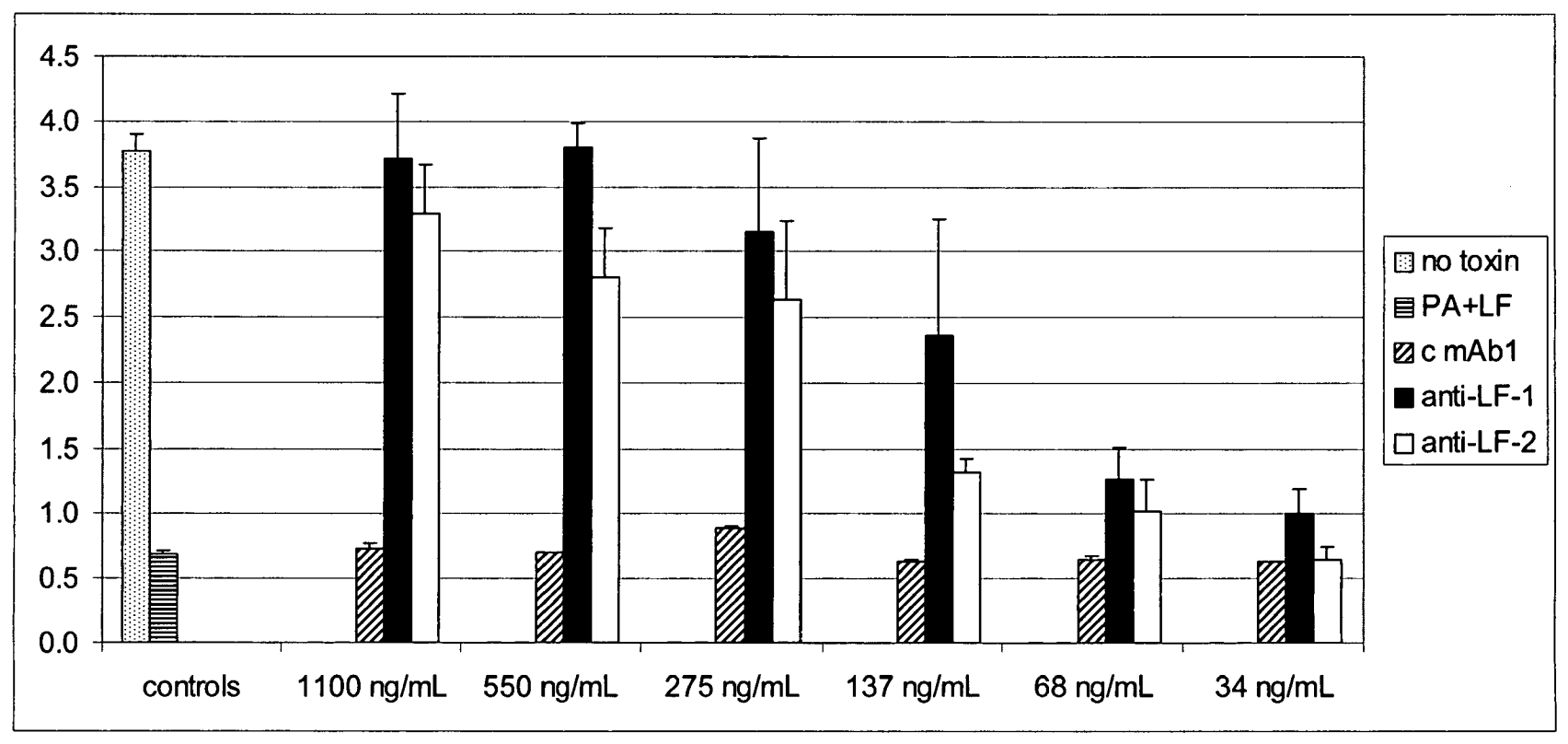

In another experiments, target cells were exposed to PA. After 1 hour LF-recognizing hMabs IQNLF-1 or IQNLF-2 and LF were added to the culture and incubated for 15 hours at 37° C. WST-1 was added and OD450 was measured at 1 hr. The results are shown in FIG. 5.

EXAMPLE 3

Figure 7:
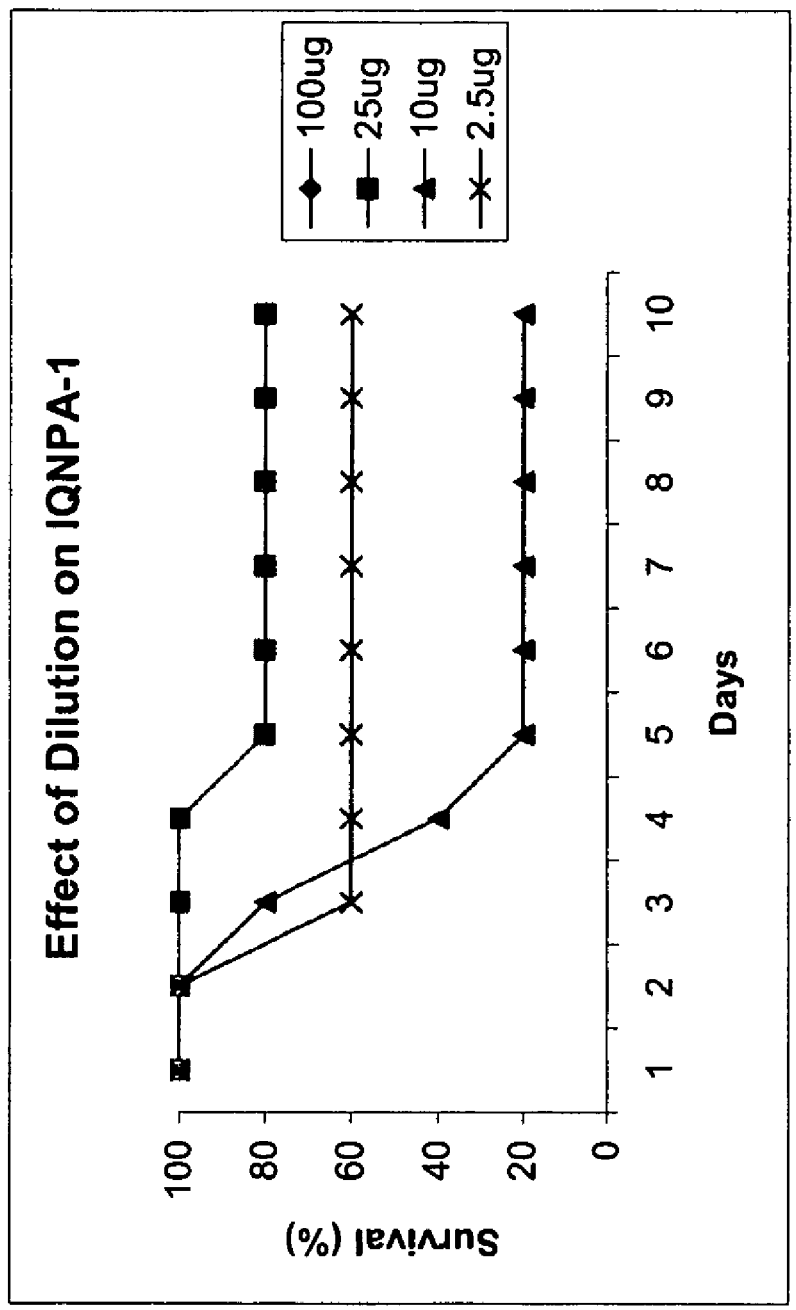
FIG. 7 is a line graph depicting the effect of dilution of IQNPA-1 on survival of mice passively immunized 2.5 hours before 30× MLD anthrax spore challenge.

In Vitro Comparison of Neutralization Activity of Human Monoclonal Antibodies against Anthrax to AVR414 Sera The toxin neutralization activity of hMabs IQNPA-1 and IQNPA-2 was compared to the activity of sera from individuals immunized with the human anthrax vaccine (AVA). This sera is designated AVA414. The assay was performed at the Center for Disease Control (Atlanta, Ga.). As shown in FIG. 7, both of hMabs IQNPA-1 and IQNPA-2 were 25× more effective in neutralizing anthrax toxin in the 99% protection assay.

EXAMPLE 4

Determination of Affinity of Human Monoclonal Antibodies against Anthrax

The binding kinetics and affinity of neutralizing hMabs IQNPA-1 and IQNPA-2 to the purified *B. anthracis* Protective Antigen were analyzed by surface plasmon resonance (BIAcore 3000, Sweden). The *B. anthracis* Protective Antigen was covalently immobilized to a CM5 sensor chip via amine group using the amine coupling kit (BIAcore) Binding kinetic parameters were measured with antibodies at different molar concentrations, and evaluated with the BIA-evaluation software. The results are shown in Table 1.

TABLE 1

| | Kinetic rates and binding affinity of HuMabs IQNPA-1 and IQNPA-2 | | | | | |
|---|---|---|---|---|---|---|
| | ka (1/Ms) | kd (1/s) | Rmax (RU) | KA (1/M) | KD (M) | Chi2 |
| IQNPA-1 | 1.6e5 | 1.93e−5 | 939 | 8.31e9 | 1.2e−10 | 89.5 |
| IQNPA-2 | 1.78e5 | 1.81e−5 | 1090 | 9.86e9 | 1.01e−10 | 211 |

EXAMPLE 5

Identification of the Epitope Recognized by the Monoclonal Antibodies against Anthrax To determine the epitopes recognized by HuMabs IQNPA-1 and IQNPA-2 were screened against domains of recominant protective antigen. The following PA domains were screened GST-1; GST1-2; GST1-2-3; GST1-2-3-4; GST3-4; and GST-4. The starting concentration of HuMabs were: IQNPA-1, 0.77 mg/ml and IQNPA-2, 0.65 mg/ml.

Briefly, one microtitre plate was coated for each domain or combination of domains. Coating concentration were determined for the molar concentration of each domain. Each Mab was assayed in duplicate at two starting dilutions of 1:1000 and 1:10 000. The assay was performed at follows:

1. Plates coated with domains (50 µl per well) and inc. O/N at 4° C.
2. Wash and block with 5% Blotto for 2hrs at 37° C.
3. Wash and add Mabs diluted 1:1000 (2 µl into 1.998 ml) and 1:10 000 (200 µl of 1:100 into 1.8 ml) in 1% Blotto. 100 µl into first two wells and serially diluted down the plate in 50 µl. Incubate overnight at 4° C.
4. Wash. Add goat anti-human IgG HRP diluted 1:6000. Incubate 1 hr at 37° C.
5. Wash. Add ABTS and read at 10, 20 and 30 minute intervals.

Plate Coating Concentrations

Full length rPA plate coating was 5 µg/ml. As it is an 83 kDa protein this equates to $6.02 \times 10^{-11}$ moles per ml. Therefore equimolar plate coatings for each domain have been calculated from their molecular weight (assuming insignificant binding of GST tag).

TABLE 2

| Domain | Mwt Daltons | Coating conc.(µg/ml) for $6.02 \times 10^{-11}$ moles/ml | Domain protein stock conc. (mg/ml) | vol. of stock required to coat one plate |
|---|---|---|---|---|
| GST 1 | 57400 | 3.45 | 4.4 | 3.9 µl in 4.9961 ml |
| GST 1 to 2 | 82600 | 4.97 | 1.6 | 15.5 µl in 4.9845 ml |
| GST 1 to 3 | 94500 | 5.69 | 0.9 | 31.6 µl in 4.9684 ml |
| GST 1 to 4 | 109000 | 6.56 | 1.3 | 25.2 µl in 4.9748 ml |
| GST 3 to 4 | 53300 | 3.21 | 4.4 | 3.6 µl in 4.9964 ml |
| GST 4 | 41400 | 2.49 | 4.6 | 2.7 µl in 4.9973 ml |

As shown in Table 3, both HuMabs only recognised the PA domains proteins containing domain 4. The assays against GST-1, 1 to 2 and 1 to 3, were repeated with previously unused plate coating proteins, at a sample starting dilution of 1:100 and with a positive control sample to determine that there was not a problem with the assay. As the end point titres for the three domain proteins containing domain 4 are approximately the same, this suggests that the HuMabs specifically bind only to the domain 4 portion of the protective antigen proteins.

TABLE 3

| Domain | End point titre | |
|---|---|---|
| | IQNPA1 | IQNPA2 |
| GST 1 | <1:100* | <1:100* |
| GST 1 to 2 | <1:100* | <1:100* |
| GST 1 to 3 | <1:100* | <1:100* |
| GST 1 to 4 | 1:256000 | 1:128000 |
| GST 3 to 4 | 1:256000 | 1:256000 |
| GST 4 | 1:256000 | 1:128000 |

*these assays repeated with Mabs at starting dilution of 1:100

EXAMPLE 6

In Vivo Evaluation of the Pre-Exposure Protective Efficacy of Human Monoclonal Antibodies against Anthrax The HuMabs, IQNPA-1 and IQNPA-2 recognized *Bacillus anthracis* protective antigen. The HuMabs have been demonstrated to neutralise the cytotoxicity induced by lethal toxin on a eukaryotic cell line in vitro. The objective of this study was to determine whether the inhibition of cytotoxicity seen in vitro correlates with protective efficacy in vivo.

The HuMabs were each administered to groups of 5 A/J mice (Harlan UK) intra-peritoneally at a standard dose of 200 µg in 0.1 ml PBS (equates to 10 mg/kg body weight, assuming 20 g mouse). A reference serum comprising pooled aliquots of rhesus macaque antiserum (animal references 221 and 224) to rPA was administered to groups of 5 mice at dose-levels of 200 µg and 500 µg, each in 0.1 ml PBS. The challenge was administered 2.5 hours after passive immunisation by the intra-peritoneal route of injection. The challenge consisted of STI strain of *B. anthracis*, given at a dose of $4.18 \times 10^4$ spores/0.1 ml.

Initial observation after immunisation showed that the mice did not react adversely to the foreign IgG administered. Each of the HuMabs administered at the 200 µg dose-level fully protected the mice against injected anthrax challenge (Table 4). The macaque reference serum conferred 40% protection at either the 200 µg or 500 µg dose-levels.

TABLE 4

Numbers of A/J mice surviving 10 days post challenge.

| Recipient Mice | Treatment Groups | | Survivors/Number Challenged (%) Day 10 |
|---|---|---|---|
| | Item | IgG Concentration (µg/mouse) | |
| 1 | IQNPA-1 | 200 | 5/5 (100) |
| 2 | IQNPA-2 | 200 | 5/5 (100) |
| 3 | Reference Item | 200 | 2/5 (40) |
| 4 | Reference Item | 500 | 2/5 (40) |
| 5 | Naive | — | 0/5 (0) |

EXAMPLE 7

In Vivo $ED_{50}$ Determination of the Human Monoclonal Antibodies against Anthrax The objective of this study was to determine the relationship between dose of HuMab administered and the protection conferred by passive transfer, in the mouse model and to identify a 50% effective dose (ED50).

The study was conducted in age-matched female A/J mice (Harlan UK). Each HuMab was titrated in a dose-response curve to determine the ED50. Each hMab was diluted as described in Table 5, to achieve the dose-levels required. Dose-levels of each hMab in the range 100 µg to 2.5 µg were administered intra-peritoneally (i.p.) to groups of 5 mice, at 2.5 hours prior to challenge with $4.64 \times 10^4$ spores/0.1 ml (approximately 30 MLD) of *B. anthracis* STI strain. A reference serum comprising pooled aliquots of rhesus macaque antiserum to rPA (animal references 221 and 224) was administered to groups of 5 A/J mice in the same dose range. The survival of mice at 10 days post-challenge was determined.

TABLE 5

Preparation of dilution series from the Test and
Reference Items to achieve the working dilutions.

| Item | Concentrations | Item (ml) | PBS (ml) | Dose |
|---|---|---|---|---|
| IQNPA-1 | 0.77 mg/ml | 1.00 | 0.54 | 100 µg/0.2 ml |
|  | 100 µg/0.2 ml | 0.50 | 0.50 | 25 µg/0.1 ml |
|  | 100 µg/0.2 ml | 0.20 | 0.80 | 10 µg/0.1 ml |
|  | 25 µg/0.1 ml | 0.10 | 0.90 | 2.5 µg/0.1 ml |
| IQNPA-2 | 0.65 mg/ml | 1.00 | 0.30 | 100 µg/0.2 ml |
|  | 100 µg/0.2 ml | 0.50 | 0.50 | 25 µg/0.1 ml |
|  | 100 µg/0.2 ml | 0.20 | 0.80 | 10 µg/0.1 ml |
|  | 25 µg/0.1 ml | 0.10 | 0.90 | 2.5 µg/0.1 ml |
| Reference - 221 | 5.92 mg/ml | 0.10 | 0.49 | 100 µg/0.1 ml |
| Reference - 224 | 6.09 mg/ml | 0.10 | 0.51 | 100 µg/0.1 ml |
| Pooled Reference Item (221 + 224) | 100 µg/0.1 ml | 0.20 | 0.60 | 25 µg/0.1 ml |
|  | 100 µg/0.1 ml | 0.10 | 0.90 | 10 µg/0.1 ml |
|  | 25 µg/0.1 ml | 0.10 | 0.90 | 2.5 µg/0.1 ml |

Figure 8:
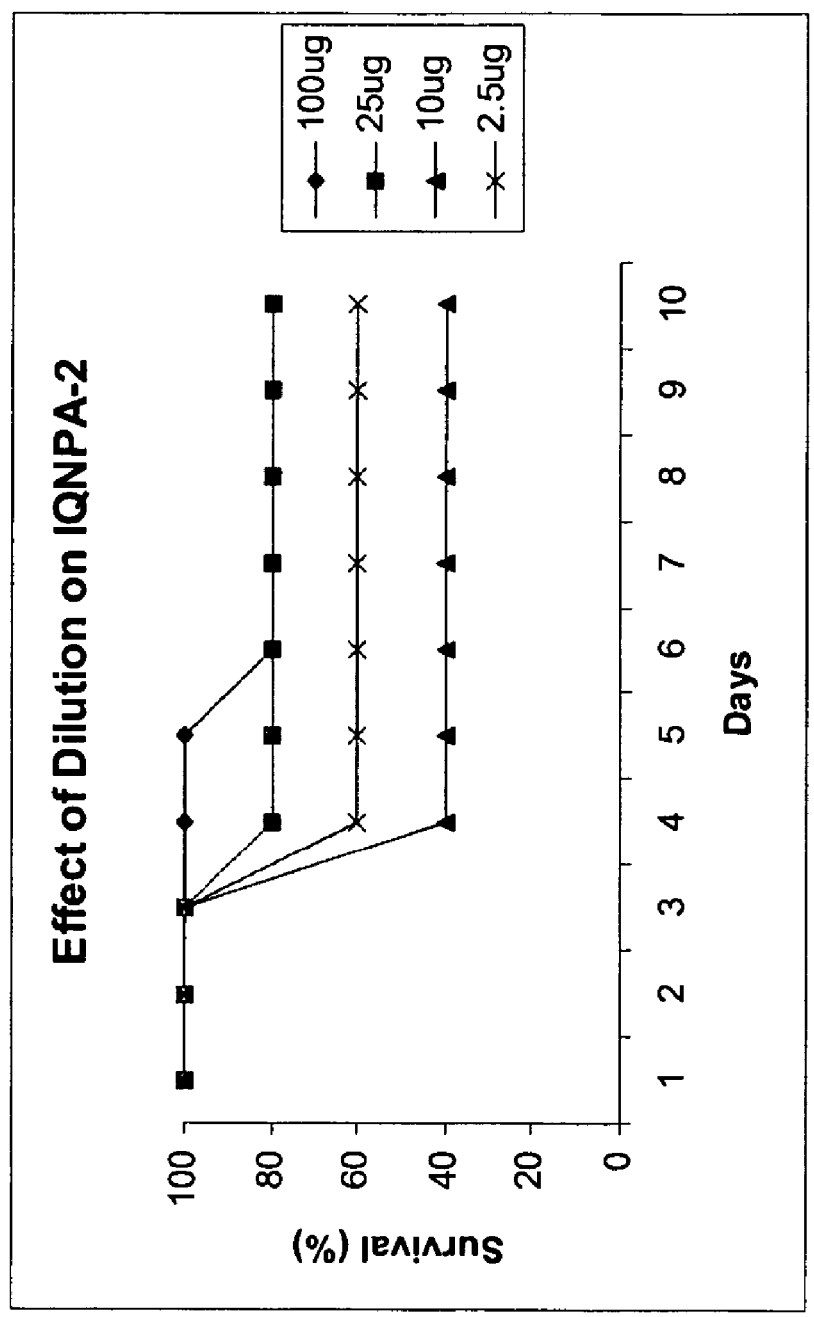
FIG. 8 is a line graph depicting the effect of dilution of IQNPA-2 on survival of mice passively immunized 2.5 hours before 30× MLD anthrax spore challenge.
Figure 9:
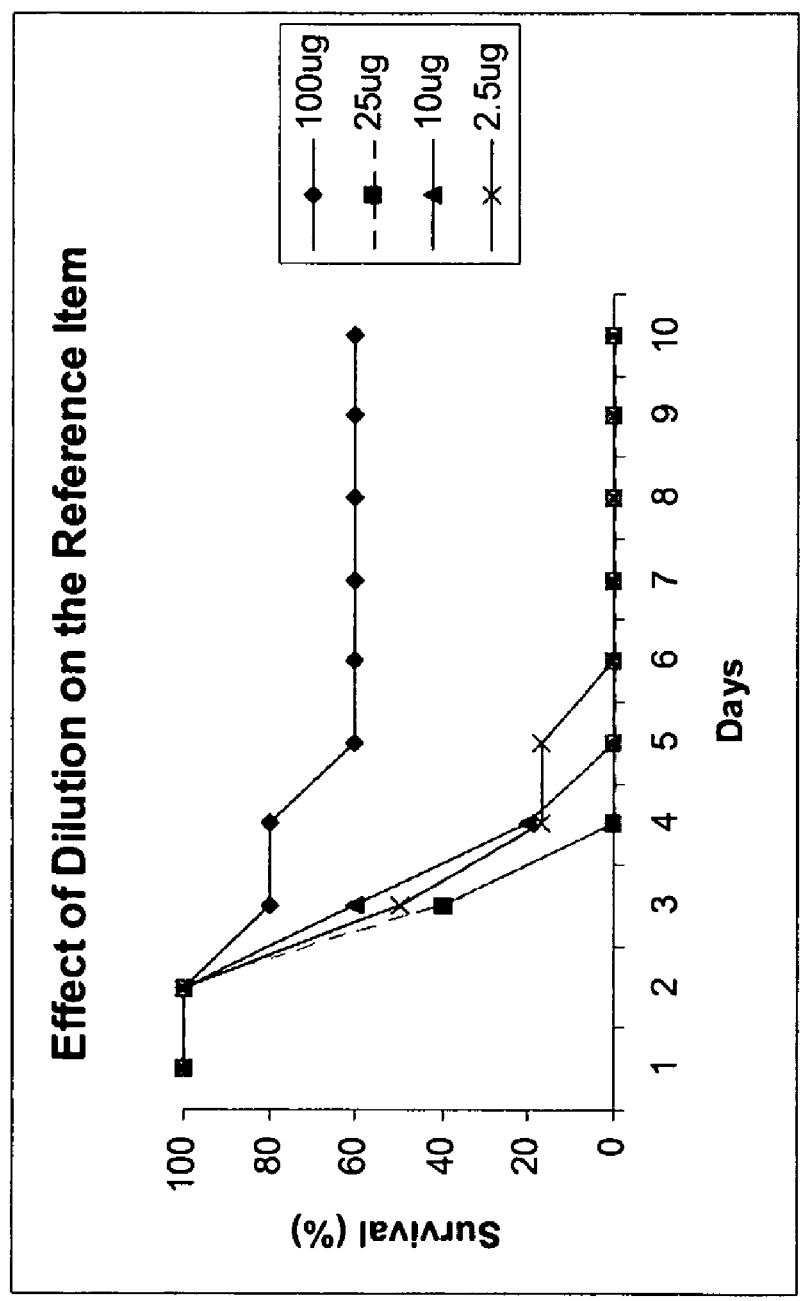
FIG. 9 is a line graph depicting the effect if dilution of Control Anthrax sera on survival of mice passively immunized 2.5 hours before 30× MLD anthrax spore challenge.
Figure 10:
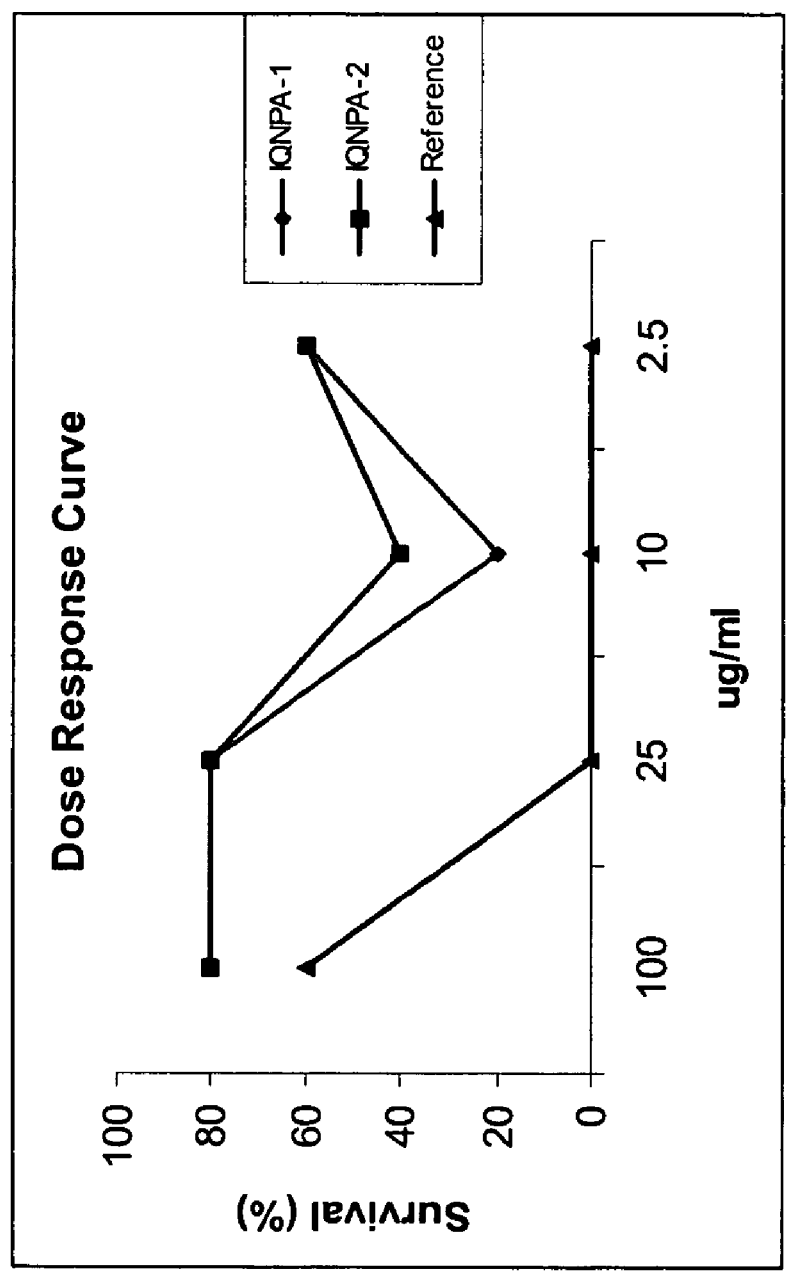
FIG. 10 is a is a line graph showing the effect of dose on survival of passively immunized mice measured until 10 days post challenge.

Initial observation after immunisation showed that the mice did not react adversely to the HuMabs, although there was a transient adverse reaction to the macaque reference serum (attributed to the urea content). All the mice had recovered prior to challenge. Protection was afforded by both HuMabs in the 10 day assay, in a dose-related manner. The protection afforded was superior to that of the reference serum which protected 60% of animals at the top dose-level (Table 6). The effect of dilution of the HuMabs and the reference serum on survival over ten days is shown in FIGS. 7-9. The HuMabs performed very similarly, with the 100 µg and 25 µg dose-levels providing 80% protection, and the 2.5 µg dose-level providing 60% protection. Suprisingly, the 10 µg dose-level of each hMAb provided the minimum protection, although the group sizes are too small to identify this as a significant different result from the 2.5 µg dose-level. A dose-response curve for survival rate for the HuMabs and the reference antiserum is shown (FIG. 10).

TABLE 6

Numbers of A/J mice surviving 10 days post challenge.

| Recipient Mice | Item | Treatment Groups IgG Concentration (µg/mouse) | Survivors/Number Challenged (%) Day 10 |
|---|---|---|---|
| 1 | IQNPA-1 | 100 | 4/5 (80) |
| 2 |  | 25 | 4/5 (80) |
| 3 |  | 10 | 1/5 (20) |
| 4 |  | 2.5 | 3/5 (60) |
| 5 | IQNPA-2 | 100 | 4/5 (80) |
| 6 |  | 25 | 4/5 (80) |
| 7 |  | 10 | 2/5 (40) |
| 8 |  | 2.5 | 3/5 (60) |
| 9 | Reference Item | 100 | 3/5 (60) |
| 10 |  | 25 | 0/5 (0) |
| 11 |  | 10 | 0/5 (0) |
| 12 |  | 2.5 | 0/5 (0) |

There was little difference in times to death for each of the HuMabs. At the 25 µg dose-level, the IQNPA-1 HuMab had a delayed time to death compared with the IQNPA-2 HuMab, but the converse held at the 100 µg dose-level.

Figure 11:
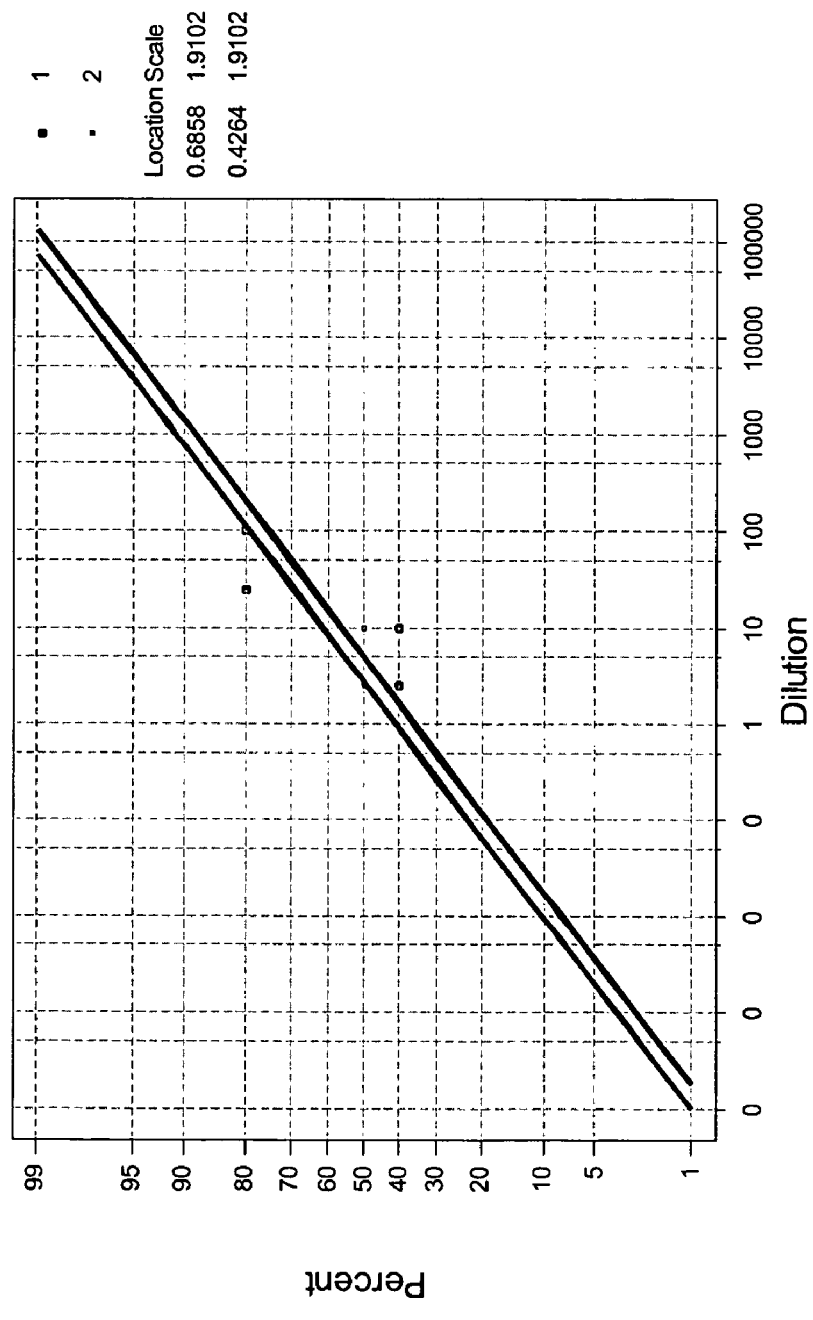
FIG. 11 is a probit graph for the HuMabs 10 days post challenge.

The assay design used in this study is a parallel line assay where the efficacy of the HuMab has been compared with the efficacy of the reference antiserum. Since the reference antiserum only protected mice at the highest dose level, the data could not be included in the statistical analysis. When the data from the HuMabs was compared for linearity, the slopes generated by titration of each HuMab did not differ significantly (p>0.05) (Table 7). Probit analysis has been carried out on the slopes for each HuMAb (FIG. 11). The ED50 values have been derived for each hMab and their relative potency has been calculated (Table 8). From this calculation, it can been seen that the IQNPA-1 HuMab is half as potent as the IQNPA-2 hMAb.

TABLE 7

Summary of statistical analysis of the
vaccine dilution slopes with P values.

| Statistical Test | P value † |
|---|---|
| Constant | 0.476 |
| Dilution | 0.144 |
| 1 compared with 2 | 0.741 |
| Equal Slopes | 0.932 |

† P value < 0.05 significantly different

TABLE 8

Calculation of ED50 values and relative potency of the HuMabs

| Item | $ED_{50}$ (µg/ml) | Relative potency IQNPA-1 vs IQNPA 2 |
|---|---|---|
| IQNPA-1 | 4.8511 | 0.5503 |
| IQNPA-2 | 2.6696 |  |

In summary, the result of this study demonstrate that both hMab's provide protection against challenge with anthrax in the mouse model. Probit analysis indicates that IQNPA-2 is twice as potent as IQNPA-1. (FIG. 11)

EXAMPLE 8

In Vivo Evaluation of the Post-Exposure Protective Efficacy of Human Monoclonal Antibodies against Anthrax The objective of this study was to determine whether the HuMabs could be efficacious when administered by a post-exposure therapy and if so, to determine the therapeutic window of post-exposure.

Figure 12:
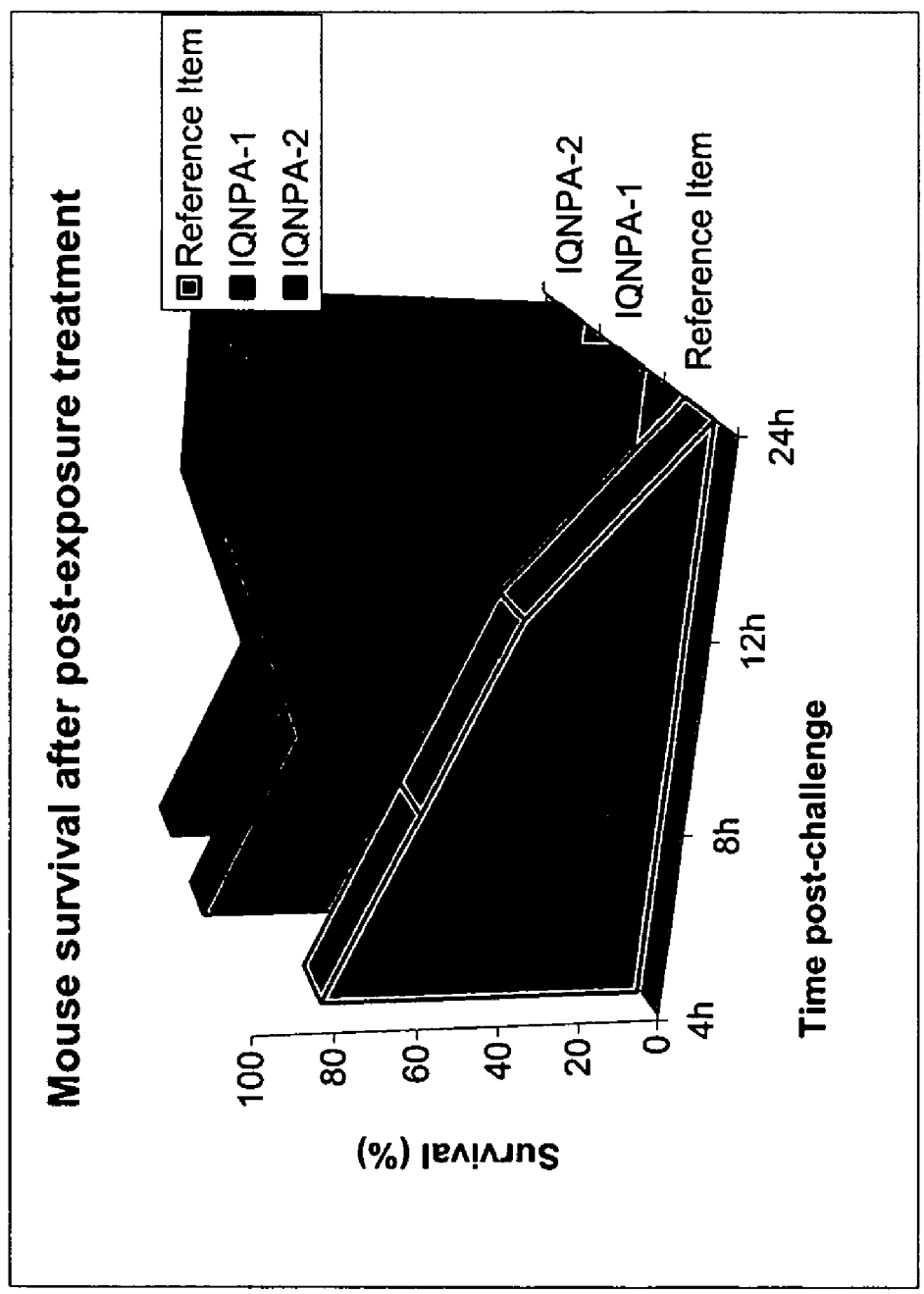
FIG. 12 is a graph showing the effect of survival of mice treated once with IQNPA-1, IQNPA-2, or control anthrax serum at different time points post challenge.

A/J mice were administered 200 µg of HuMab intra-peritoneally at 4 hours, 8 hours, 12 hours and 24 hours post exposure to the STI strain of *B. anthracis*, given at a dose of $5.6 \times 10^4$ spores/0.1 ml, equivalent to approximately 40 median lethal doses (MLD). As shown in Table 9 and FIG. 12, protection against infection was afforded by both HuMabs. The slight breakthrough that was observed at days 10 and 20 in the groups dosed with IQNPA2 and IQNPA1 respectively at 8 h post-challenge is not significant (1 animal out of 5).

The HuMab IQNPA antibodies tested did not differ significantly from one another in the protection conferred on recipient mice by passive transfer. Both IQNPA1 and IQNPA2 are protective in the mouse model when given at up to 24 h post exposure to *B. anthracis* STI strain and protection was maintained over 20 days post-exposure, when titres of the passively transferred antibodies would be expected to be in decline. The Reference Item offered less protection to the mice over time.

In summary, these studies demonstrated that the fully human monoclonal antibodies IQNPA-1 and 2 are useful drugs for the post-exposure and prophylactic treatment of anthrax.

TABLE 9

Numbers of A/J mice surviving 20 days post challenge.

| Recipient Mice Cage No (n = 5) | Treatment Groups | Treatment time post exposure | Survivors/Number Challenged (%) Day 10 | Survivors/Number Challenged (%) Day 20 |
|---|---|---|---|---|
| 1 | IQNPA-1 | +4 h | 5/5 | 5/5 |
| 2 | 200 μg/mouse | +8 h | 5/5 | 4/5 |
| 3 | | +12 h | 5/5 | 5/5 |
| 4 | | +24 h | 5/5 | 5/5 |
| 5 | IQNPA-2 | +4 h | 5/5 | 5/5 |
| 6 | 200 μg/mouse | +8 h | 4/5 | 4/5 |
| 7 | | +12 h | 5/5 | 5/5 |
| 8 | | +24 h | 5/5 | 5/5 |
| 9 | Reference Item | +4 h | 4/5 | 4/5 |
| 10 | (Pooled samples | +8 h | 4/5 | 3/5 |
| 11 | 221 + 224) | +12 h | 3/5 | 2/5 |
| 12 | | +24 h | 1/5 | 0/5 |

TABLE 10

Numbers of A/J mice surviving 10 days post challenge.

| Recipient Mice Cage No (n = 5) | Treatment Groups | Treatment time post exposure | Survivors/Number Challenged (%) Day 10 |
|---|---|---|---|
| 1 | IQNPA-2 | +24 h | 5/5 |
| 2 | 180 μg/mouse | +36 h | 5/5 |
| 3 | | +48 h | 3/5 |
| 4 | IQNPA-2 | +4 h | 4/5 |
| 5 | 100 μg/mouse | +8 h | 5/5 |
| 6 | | +12 h | 5/5 |
| 7 | | +24 h | 5/5 |
| 8 | | +36 h | 2/5 |
| 9 | | +48 h | 3/5 |
| 10 | Reference Item | +8 h | 3/5 |
| 11 | (Pooled samples | +12 h | 2/5 |
| 12 | 221 + 224) | +24 h | 1/5 |

Figure 13:
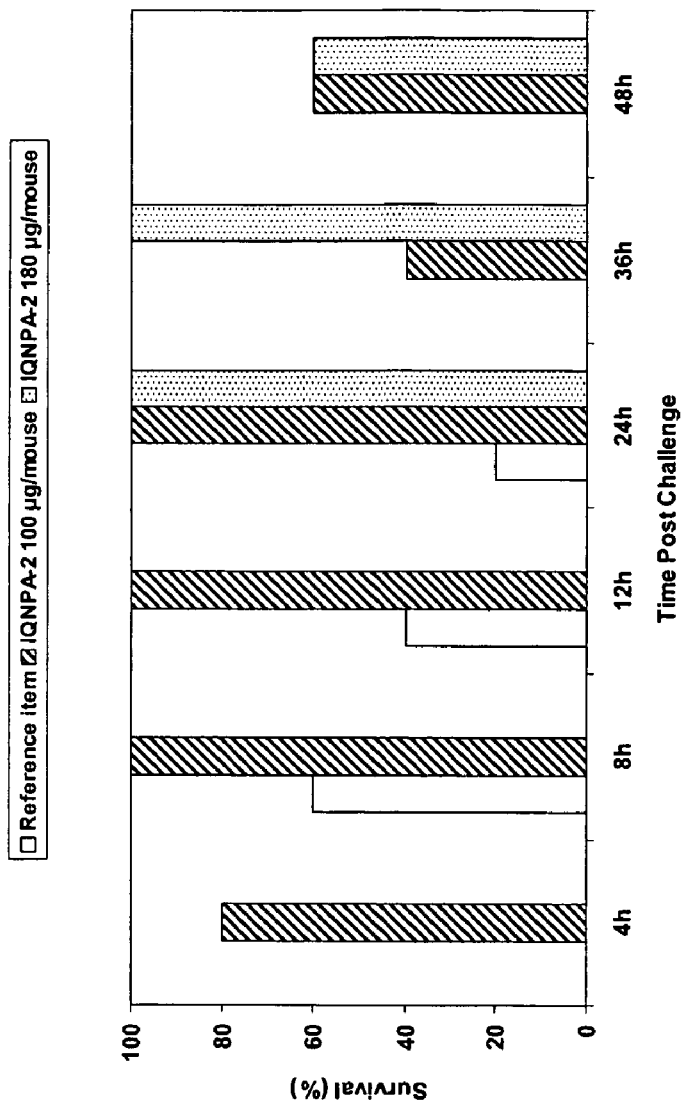
FIG. 13 is a graph showing the effect of survival of mice treated once with IQNPA-2, or control anthrax serum at different time points post challenge.

In a second study A/J mice were administered 180 μg of HuMab intra-peritoneally at 24 hours, 36 hours, and 48 hours or 1000 μg of HuMab intra-peritoneally at 4 hours, 8 hours, 12 hours, and 24 hours post exposure to the STI strain of *B. anthracis*, given at a dose of $3.4 \times 10^4$ spores/0.1 ml, equivalent to approximately 25 median lethal doses (MLD). As shown in Table 10 and FIG. 13, protection against infection was afforded by IQNPA-2 over 10 days post-challenge. Total protection was observed with the mice dosed with 100 μg of the Test Item at 24 hours post challenge. Total protection was extended to 36 hours post challenge when the mice were dosed with 180 μg of the Test Item (Table 10). FIG. 13 shows the effect on mouse survival when vaccinated at different timepoints post challenge. The Reference Item offered less protection to the mice over time.

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications considered to be within the scope of the following claims. The claims presented are representative of the inventions disclosed herein.

We claim:

1. An isolated fully human monoclonal antibody, or antigen-binding fragment thereof, comprising a heavy chain variable (VH) domain and a light chain variable (VL) domain, wherein the VH domain and the VL domain each comprise three complementarity determining regions 1 to 3 (CDR1-3), and wherein each CDR comprises the following amino acid sequences: VH CDR1: VQPGG (SEQ ID NO:17); VH CDR2: SYAMSWVRQAPGKGLEW (SEQ ID NO:18); VH CDR3: YMQMNSL (SEQ ID NO:19); VL CDR1: TQSPDFQSVSP (SEQ ID NO:20); VL CDR2: SSLHWYQ (SEQ ID NO:21); and VL CDR3: DFTLTINSL (SEQ ID NO:22); and wherein said antibody binds to an epitope on a region of the lethal factor polypeptide of *Bacillus anthracis*.

2. An isolated antibody comprising a heavy chain comprising a polypeptide encoded by the nucleotide sequence of SEQ ID NO:5 and a light chain comprising a polypeptide encoded by the nucleotide sequence of SEQ ID NO:7, wherein the antibody binds lethal factor polypeptide and neutralizes *Bacillus anthracis* lethal toxin.

3. An isolated antibody comprising a heavy chain comprising the amino acid sequence of SEQ ID NO: 6 and a light chain comprising the amino acid sequence SEQ ID NO: 8, wherein the antibody binds lethal factor polypeptide and neutralizes *Bacillus anthracis* lethal toxin.

4. The monoclonal antibody of claim 1, wherein said monoclonal antibody comprises the amino acid sequences of SEQ ID NO: 6 and SEQ ID NO: 8.

5. A pharmaceutical composition comprising the monoclonal antibody of claim 1 or 4, and a pharmaceutically acceptable carrier.

6. The pharmaceutical composition of claim 5, further comprising a second monoclonal antibody, wherein the second monoclonal antibody binds to the *Bacillus anthracis* protective antigen.

7. The pharmaceutical composition of claim 6, wherein the second monoclonal antibody comprises the amino acid sequences of SEQ ID NOs: 2 and 4.

8. A passive vaccine against *Bacillus anthracis*, comprising the pharmaceutical composition of claim 5.

9. A kit comprising, in one or more containers, the monoclonal antibody of claim 1 or 4.

10. An isolated cell producing an antibody comprising one or more polynucleotides which encode the polypeptides of SEQ ID NOs: 6 and 8, wherein the polypeptides encode an antibody that binds lethal factor polypeptide and neutralizes *Bacillus anthracis* lethal toxin.

* * * * *

UNITED STATES PATENT AND TRADEMARK OFFICE
CERTIFICATE OF CORRECTION

PATENT NO. : 7,658,925 B2  Page 1 of 1
APPLICATION NO. : 11/072102
DATED : February 9, 2010
INVENTOR(S) : Groen et al.

It is certified that error appears in the above-identified patent and that said Letters Patent is hereby corrected as shown below:

On the title page,

[*] Notice:   Subject to any disclaimer, the term of this patent is extended or adjusted under 35 U.S.C. 154(b) by 615 days Delete the phrase "by 615 days" and insert -- by 1055 days --

Signed and Sealed this

Sixth Day of July, 2010

David J. Kappos
*Director of the United States Patent and Trademark Office*

SEQUENCE LISTING

<160> NUMBER OF SEQ ID NOS: 22

<210> SEQ ID NO 1
<211> LENGTH: 1432
<212> TYPE: DNA
<213> ORGANISM: Homo sapiens

<400> SEQUENCE: 1

```
ggcccagccg gccatggact ggatctggag gatcctcttt ttggtggcag cagccacagg      60
tgcccactcc caggtccagc ttgtgcagtc tggggctgag gtgaagaagc ctggggcctc     120
agtgaaggtt tcctgcaagg cctctggata caccttcact agcaatgcta tacaatgggt     180
gcgccaggcc cccggacaaa ggcttgagtg ggtgggatgg atcaacggtg gcgatggtaa     240
cacaaaatat tcacagaagt tccagggcag agtcaccatt agtagggaca tatccgcgag     300
cacagcctac atggagctga gcagcctgag atctgaagac acggctgtgt attactgtgc     360
gagacatcgt ttgcaaagag gggggttcga cccctgggc cagggaaccc tggtcaccgt     420
ctcctcagcc tccaccaagg gcccatcggt cttccccctg gcaccttcct ccaagagcac     480
ctctgggggc acagcggccc tgggctgcct ggtcaaggac tacttccccg aaccggtgac     540
ggtgtcgtgg aactcaggcg ccctgaccag cggcgtgcac accttcccgg ctgtcctaca     600
gtcctcagga ctctactccc tcagcagcgt ggtgaccgtg ccctccagca gcttgggcac     660
ccagacctac atctgcaacg tgaatcacaa gcccagcaac accaaggtgg acaagagagt     720
```

-continued

```
tgagcccaaa tcttgtgaca aaactcacac atgcccaccg tgcccagcac ctgaactcct    780
gggggggaccg tcagtcttcc tcttcccccc aaaacccaag dacaccctca tgatctcccg    840
gacccctgag gtcacatgcg tggtggtgga cgtgagccac gaagaccctg aggtcaagtt    900
caactggtac gtggacggcg tggaggtgca taatgccaag acaaagccgc gggaggagca    960
gtacaacagc acgtaccgtg tggtcagcgt cctcaccgtc ctgcaccagg actggctgaa   1020
tggcaaggag tacaagtgca aggtctccaa caaagccctc ccagccccca tcgagaaaac   1080
catctccaaa gccaaagggc agccccgaga accacaggtg tacaccctgc ccccatcccg   1140
ggaggagatg accaagaacc aggtcagcct gacctgcctg gtcaaaggct tctatcccag   1200
cgacatcgcc gtggagtggg agagcaatgg gcagccggag aacaactaca agaccacgcc   1260
tcccgtgctg gactccgacg gctccttctt cctctatagc aagctcaccg tggacaagag   1320
caggtggcag caggggaacg tcttctcatg ctccgtgatg catgaggctc tgcacaacca   1380
ctacacgcag aagagcctct ccctgtctcc gggtaaatga ggcctccgag gc           1432
```

<210> SEQ ID NO 2
<211> LENGTH: 468
<212> TYPE: PRT
<213> ORGANISM: Homo sapiens

<400> SEQUENCE: 2

```
Met Asp Trp Ile Trp Arg Ile Leu Phe Leu Val Ala Ala Ala Thr Gly
 1               5                  10                  15

Ala His Ser Gln Val Gln Leu Val Gln Ser Gly Ala Glu Val Lys Lys
             20                  25                  30

Pro Gly Ala Ser Val Lys Val Ser Cys Lys Ala Ser Gly Tyr Thr Phe
         35                  40                  45

Thr Ser Asn Ala Ile Gln Trp Val Arg Gln Ala Pro Gly Gln Arg Leu
     50                  55                  60

Glu Trp Val Gly Trp Ile Asn Gly Gly Asp Gly Asn Thr Lys Tyr Ser
 65                  70                  75                  80

Gln Lys Phe Gln Gly Arg Val Thr Ile Ser Arg Asp Ile Ser Ala Ser
                 85                  90                  95

Thr Ala Tyr Met Glu Leu Ser Ser Leu Arg Ser Glu Asp Thr Ala Val
            100                 105                 110

Tyr Tyr Cys Ala Arg His Arg Leu Gln Arg Gly Gly Phe Asp Pro Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Arg Val Glu Pro Lys Ser
225                 230                 235                 240

Cys Asp Lys Thr His Thr Cys Pro Pro Cys Pro Ala Pro Glu Leu Leu
```

```
                245                 250                 255
Gly Gly Pro Ser Val Phe Leu Phe Pro Pro Lys Pro Lys Asp Thr Leu
            260                 265                 270

Met Ile Ser Arg Thr Pro Glu Val Thr Cys Val Val Val Asp Val Ser
            275                 280                 285

His Glu Asp Pro Glu Val Lys Phe Asn Trp Tyr Val Asp Gly Val Glu
            290                 295                 300

Val His Asn Ala Lys Thr Lys Pro Arg Glu Glu Gln Tyr Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Ala Leu Pro Ala Pro
            340                 345                 350

Ile Glu Lys Thr Ile Ser Lys Ala Lys Gly Gln Pro Arg Glu Pro Gln
            355                 360                 365

Val Tyr Thr Leu Pro Pro Ser Arg Glu Glu Met Thr Lys Asn Gln Val
            370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Lys Leu Thr
            420                 425                 430

Val Asp Lys Ser Arg Trp Gln Gln Gly Asn Val Phe Ser Cys Ser Val
            435                 440                 445

Met His Glu Ala Leu His Asn His Tyr Thr Gln Lys Ser Leu Ser Leu
450                 455                 460

Ser Pro Gly Lys
465

<210> SEQ ID NO 3
<211> LENGTH: 733
<212> TYPE: DNA
<213> ORGANISM: Homo sapiens

<400> SEQUENCE: 3
ggcccagccg gccatggaag ccccagcgca gcttctcttc ctcctgctac tctggctccc      60
agataccacc ggagaaattg tgttgacgca gtctccaggc accctgtctt tgtctccagg     120
ggaaagagcc accctctcct gcagggccag tcagagtgtt agctacagct ccttagcctg     180
gtaccagcag aaacctggcc aggctcccag cctcctcatc tatggtgcat ccagcagggc     240
cactggcatc ccagacaggt tcagtggcag tgggtctggg ccagacttca ctctcaccat     300
cagcagactg gagcctgaag attttgcagt ttattactgt cagcactatg gtaactcacc     360
gtacactttt ggccagggga ccaagctgga gatcaaacga actgtggctg caccatctgt     420
cttcatcttc ccgccatctg atgagcagtt gaaatctgga actgcctctg ttgtgtgcct     480
gctgaataac ttctatccca gagaggccaa agtacagtgg aaggtggata acgcctcca     540 atcgggtaac tcccaggaga gtgtcacaga gcaggacagc aaggacagca cctacagcct     600
cagcagcacc ctgacgctga gcaaagcaga ctacgagaaa cacaaagtct acgcctgcga     660
agtcacccat cagggcctga gctcgcccgt cacaaagagc ttcaacaggg gagagtgtta     720
gggcctccga ggc                                                        733
```

<210> SEQ ID NO 4
<211> LENGTH: 235
<212> TYPE: PRT
<213> ORGANISM: Homo sapiens

<400> SEQUENCE: 4

```
Met Glu Ala Pro Ala Gln Leu Leu Phe Leu Leu Leu Leu Trp Leu Pro
 1               5                  10                  15
Asp Thr Thr Gly Glu Ile Val Leu Thr Gln Ser Pro Gly Thr Leu Ser
            20                  25                  30
Leu Ser Pro Gly Glu Arg Ala Thr Leu Ser Cys Arg Ala Ser Gln Ser
        35                  40                  45
Val Ser Tyr Ser Ser Leu Ala Trp Tyr Gln Gln Lys Pro Gly Gln Ala
    50                  55                  60
Pro Ser Leu Leu Ile Tyr Gly Ala Ser Ser Arg Ala Thr Gly Ile Pro
65                  70                  75                  80
Asp Arg Phe Ser Gly Ser Gly Ser Gly Pro Asp Phe Thr Leu Thr Ile
                85                  90                  95
Ser Arg Leu Glu Pro Glu Asp Phe Ala Val Tyr Tyr Cys Gln His Tyr
            100                 105                 110
Gly Asn Ser Pro Tyr Thr Phe Gly Gln Gly Thr Lys Leu Glu Ile Lys
        115                 120                 125
Arg Thr Val Ala Ala Pro Ser Val Phe Ile Phe Pro Pro Ser Asp Glu
    130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235
```

<210> SEQ ID NO 5
<211> LENGTH: 1438
<212> TYPE: DNA
<213> ORGANISM: Homo sapiens

<400> SEQUENCE: 5

| | | | | | |
|---|---|---|---|---|---|
| ggcccagccg | gccatggagt | tgggctgtg | ctggctttt | cttgtggcta | ttttaaaagg | 60 |
| tgtccagtgt | gaggtgcagc | tgttggagtc | tgggggaggc | ttggtacagc | cggggggtc | 120 |
| cctgagactc | tcctgttctg | gctctggatt | catgtttagc | agttatgcca | tgagctgggt | 180 |
| ccgccaggct | ccagggaagg | ggctggagtg | ggtctcagga | attagtggta | gcggtggtac | 240 |
| tacaaactac | gcagactccg | tgaagggccg | gttcaccatc | tccagagaca | attccaagaa | 300 |
| cacgctgtat | atgcaaatga | acagcctgag | agccgaggac | acggccgtat | attactgtgc | 360 |
| gaaagatggg | gtatatggcc | gactgggggg | ttctgactac | tggggccagg | gaaccctggt | 420 |
| caccgtctcc | tcagcctcca | ccaagggccc | atcagtcttc | cccctggcac | cctcctccaa | 480 |
| gagcacctct | gggggcacag | cggccctggg | ctgcctggtc | aaggactact | tccccgaacc | 540 |
| ggtgacggtg | tcgtggaact | caggcgccct | gaccagcggc | gtgcacacct | tcccggctgt | 600 |

```
cctacagtcc tcaggactct actccctcag cagcgtggtg accgtgccct ccagcagctt      660
gggcacccag acctacatct gcaacgtgaa tcacaagccc agcaacacca aggtggacaa      720
gaaagttgag cccaaatctt gtgacaaaac tcacacatgc ccaccgtgcc cagcacctga      780
actcctgggg ggaccgtcag tcttcctctt ccccccaaaa cccaaggaca ccctcatgat      840
ctcccggacc cctgaggtca catgcgtggt ggtggacgtg agccacgaag accctgaggt      900
caagttcaac tggtacgtgg acggcgtgga ggtgcataat gccaagacaa agccgcggga      960
ggagcagtac aacagcacgt accgtgtggt cagcgtcctc accgtcctgc accaggactg     1020
gctgaatggc aaggagtaca agtgcaaggt ctccaacaaa gccctcccag cccccatcga     1080
gaaaaccatc tccaaagcca agggcagccc cgagaaccag gtgtacaccc tgcccccc      1140 atcccgggat gagctgacca agaaccaggt cagcctgacc tgcctggtca aaggcttcta     1200
tcccagcgac atcgccgtgg agtgggagag caatgggcag ccggagaaca actacaagac     1260
cacgcctccc gtgctggact ccgacggctc cttcttcctc tacagcaagc tcaccgtgga     1320
caagagcagg tggcagcagg ggaacgtctt ctcatgctcc gtgatgcatg agggtctgca     1380
caaccactac acgcagaaga gcctctccct gtctccgggt aaatgaggcc tccgaggc       1438
```

<210> SEQ ID NO 6
<211> LENGTH: 470
<212> TYPE: PRT
<213> ORGANISM: Homo sapiens

<400> SEQUENCE: 6

```
Met Glu Leu Gly Leu Cys Trp Leu Phe Leu Val Ala Ile Leu Lys Gly
1               5                   10                  15

Val Gln Cys Glu Val Gln Leu Leu Glu Ser Gly Gly Gly Leu Val Gln
            20                  25                  30

Pro Gly Gly Ser Leu Arg Leu Ser Cys Ser Gly Ser Gly Phe Met Phe
        35                  40                  45

Ser Ser Tyr Ala Met Ser Trp Val Arg Gln Ala Pro Gly Lys Gly Leu
    50                  55                  60

Glu Trp Val Ser Gly Ile Ser Gly Ser Gly Gly Thr Thr Asn Tyr Ala
65                  70                  75                  80

Asp Ser Val Lys Gly Arg Phe Thr Ile Ser Arg Asp Asn Ser Lys Asn
                85                  90                  95

Thr Leu Tyr Met Gln Met Asn Ser Leu Arg Ala Glu Asp Thr Ala Val
            100                 105                 110

Tyr Tyr Cys Ala Lys Asp Gly Val Tyr Gly Arg Leu Gly Gly Ser Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220
```

```
Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Gly Leu His Asn His Tyr Thr Gln Lys Ser Leu
    450                 455                 460

Ser Leu Ser Pro Gly Lys
465                 470

<210> SEQ ID NO 7
<211> LENGTH: 727
<212> TYPE: DNA
<213> ORGANISM: Homo sapiens

<400> SEQUENCE: 7
ggcccagccg gccatgttgc catcacaact cattgggttt ctgctgctct gggttccagc      60
ctccaggggt gaaattgtgc tgactcagtc tccagacttt cagtctgtga gtccaaagga    120
gaaagtcacc atcacctgcc gggccagcca gagcgttggt agtagcttac actggtacca    180
gcagaaacca gatcagtctc caaagctcct catcaagtat gcttcccagt ccttctcagg    240
ggtcccctcg aggttcagtg gcagtggatc tgggacagat ttcacccctca ccatcaatag    300 cctggaaact gaagatgctg caacgtatta ctgtcatcag agtagtagtt acctctcac    360 tttcggcgga gggaccaagg tggagatcaa acgaactgtg gctgcaccat ctgtcttcat    420
cttcccgcca tctgatgagc agttgaaatc tggaactgcc tctgttgtgt gcctgctgaa    480
taacttctat cccagagagg ccaaagtaca gtggaaggtg gataacgccc tccaatcggg    540
taactcccag gagagtgtca cagagcagga cagcaaggac agcacctaca gcctcagcag    600
caccctgacg ctgagcaaag cagactacga gaaacacaaa gtctacgcct gcgaagtcac    660
ccatcagggc ctgagctcgc ccgtcacaaa gagcttcaac aggggagagt gttagggcct    720
``` ccgaggc 727

<210> SEQ ID NO 8
<211> LENGTH: 233
<212> TYPE: PRT
<213> ORGANISM: Homo sapiens

<400> SEQUENCE: 8

Met Leu Pro Ser Gln Leu Ile Gly Phe Leu Leu Trp Val Pro Ala
1               5                   10                  15

Ser Arg Gly Glu Ile Val Leu Thr Gln Ser Pro Asp Phe Gln Ser Val
            20                  25                  30

Ser Pro Lys Glu Lys Val Thr Ile Thr Cys Arg Ala Ser Gln Ser Val
        35                  40                  45

Gly Ser Ser Leu His Trp Tyr Gln Gln Lys Pro Asp Gln Ser Pro Lys
    50                  55                  60

Leu Leu Ile Lys Tyr Ala Ser Gln Ser Phe Ser Gly Val Pro Ser Arg
65                  70                  75                  80

Phe Ser Gly Ser Gly Ser Gly Thr Asp Phe Thr Leu Thr Ile Asn Ser
                85                  90                  95

Leu Glu Thr Glu Asp Ala Ala Thr Tyr Tyr Cys His Gln Ser Ser Ser
            100                 105                 110

Leu Pro Leu Thr Phe Gly Gly Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 9
<211> LENGTH: 135
<212> TYPE: PRT
<213> ORGANISM: Homo sapiens

<400> SEQUENCE: 9

Asn Asn Ile Ala Val Gly Ala Asp Glu Ser Val Val Lys Glu Ala His
1               5                   10                  15

Arg Glu Val Ile Asn Ser Ser Thr Glu Gly Leu Leu Leu Asn Ile Asp
            20                  25                  30

Lys Asp Ile Arg Lys Ile Leu Ser Gly Tyr Ile Val Glu Ile Glu Asp
        35                  40                  45

Thr Glu Gly Leu Lys Glu Val Ile Asn Asp Arg Tyr Asp Met Leu Asn
    50                  55                  60

Ile Ser Ser Leu Arg Gln Asp Gly Lys Thr Phe Ile Asp Phe Lys Lys
65                  70                  75                  80

```
Tyr Asn Asp Lys Leu Pro Leu Tyr Ile Ser Asn Pro Asn Tyr Lys Val
            85                  90                  95

Asn Val Tyr Ala Val Thr Lys Glu Asn Thr Ile Ile Asn Pro Ser Glu
            100                 105                 110

Asn Gly Asp Thr Ser Thr Asn Gly Ile Lys Lys Ile Leu Ile Phe Ser
            115                 120                 125

Lys Lys Gly Tyr Glu Ile Gly
            130                 135

<210> SEQ ID NO 10
<211> LENGTH: 164
<212> TYPE: PRT
<213> ORGANISM: Homo sapiens

<400> SEQUENCE: 10

Thr Asn Ile Tyr Thr Val Leu Asp Lys Ile Lys Leu Asn Ala Lys Met
1               5                   10                  15

Asn Ile Leu Ile Arg Asp Lys Arg Phe His Tyr Asp Arg Asn Asn Ile
            20                  25                  30

Ala Val Gly Ala Asp Glu Ser Val Val Lys Glu Ala His Arg Glu Val
            35                  40                  45

Ile Asn Ser Ser Thr Glu Gly Leu Leu Leu Asn Ile Asp Lys Asp Ile
        50                  55                  60

Arg Lys Ile Leu Ser Gly Tyr Ile Val Glu Ile Glu Asp Thr Glu Gly
65                  70                  75                  80

Leu Lys Glu Val Ile Asn Asp Arg Tyr Asp Met Leu Asn Ile Ser Ser
            85                  90                  95

Leu Arg Gln Asp Gly Lys Thr Phe Ile Asp Phe Lys Lys Tyr Asn Asp
            100                 105                 110

Lys Leu Pro Leu Tyr Ile Ser Asn Pro Asn Tyr Lys Val Asn Val Tyr
            115                 120                 125

Ala Val Thr Lys Glu Asn Thr Ile Ile Asn Pro Ser Glu Asn Gly Asp
            130                 135                 140

Thr Ser Thr Asn Gly Ile Lys Lys Ile Leu Ile Phe Ser Lys Lys Gly
145                 150                 155                 160

Tyr Glu Ile Gly

<210> SEQ ID NO 11
<211> LENGTH: 5
<212> TYPE: PRT
<213> ORGANISM: Homo sapiens

<400> SEQUENCE: 11

Lys Lys Pro Gly Ala
1               5

<210> SEQ ID NO 12
<211> LENGTH: 17
<212> TYPE: PRT
<213> ORGANISM: Homo sapiens

<400> SEQUENCE: 12

Ser Asn Ala Ile Gln Trp Val Arg Gln Ala Pro Gly Gln Arg Leu Glu
1               5                   10                  15

Trp

<210> SEQ ID NO 13
<211> LENGTH: 8
```

<212> TYPE: PRT
<213> ORGANISM: Homo sapiens

<400> SEQUENCE: 13

Tyr Met Glu Leu Ser Ser Leu Arg
1               5

<210> SEQ ID NO 14
<211> LENGTH: 11
<212> TYPE: PRT
<213> ORGANISM: Homo sapiens

<400> SEQUENCE: 14

Leu Thr Gln Ser Pro Gly Thr Leu Ser Leu Ser
1               5                   10

<210> SEQ ID NO 15
<211> LENGTH: 7
<212> TYPE: PRT
<213> ORGANISM: Homo sapiens

<400> SEQUENCE: 15

Ser Tyr Ser Ser Leu Ala Trp
1               5

<210> SEQ ID NO 16
<211> LENGTH: 9
<212> TYPE: PRT
<213> ORGANISM: Homo sapiens

<400> SEQUENCE: 16

Gly Pro Asp Phe Thr Leu Thr Ile Ser
1               5

<210> SEQ ID NO 17
<211> LENGTH: 5
<212> TYPE: PRT
<213> ORGANISM: Homo sapiens

<400> SEQUENCE: 17

Val Gln Pro Gly Gly
1               5

<210> SEQ ID NO 18
<211> LENGTH: 17
<212> TYPE: PRT
<213> ORGANISM: Homo sapiens

<400> SEQUENCE: 18

Ser Tyr Ala Met Ser Trp Val Arg Gln Ala Pro Gly Lys Gly Leu Glu
1               5                   10                  15

Trp

<210> SEQ ID NO 19
<211> LENGTH: 7
<212> TYPE: PRT
<213> ORGANISM: Homo sapiens

<400> SEQUENCE: 19

Tyr Met Gln Met Asn Ser Leu
1               5

<210> SEQ ID NO 20
<211> LENGTH: 11

-continued

```
<212> TYPE: PRT
<213> ORGANISM: Homo sapiens

<400> SEQUENCE: 20

Thr Gln Ser Pro Asp Phe Gln Ser Val Ser Pro
1               5                   10

<210> SEQ ID NO 21
<211> LENGTH: 7
<212> TYPE: PRT
<213> ORGANISM: Homo sapiens

<400> SEQUENCE: 21

Ser Ser Leu His Trp Tyr Gln
1               5

<210> SEQ ID NO 22
<211> LENGTH: 9
<212> TYPE: PRT
<213> ORGANISM: Homo sapiens

<400> SEQUENCE: 22

Asp Phe Thr Leu Thr Ile Asn Ser Leu
1               5
```